United States Patent
Ahn et al.

(10) Patent No.: US 11,162,121 B2
(45) Date of Patent: Nov. 2, 2021

(54) METHOD FOR PRODUCING MEDIUM CHAIN DIAMINE

(71) Applicant: KOREA RESEARCH INSTITUTE OF BIOSCIENCE AND BIOTECHNOLOGY, Daejeon (KR)

(72) Inventors: Jung Oh Ahn, Daejeon (KR); Hong Weon Lee, Daejeon (KR); Gyu Yeon Park, Daejeon (KR); Hee Suk Lee, Daejeon (KR); Min Jeong Jang, Daejeon (KR); Woo Young Jeon, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 45 days.

(21) Appl. No.: 15/771,830

(22) PCT Filed: Oct. 27, 2016

(86) PCT No.: PCT/KR2016/012174
§ 371 (c)(1),
(2) Date: Jun. 22, 2018

(87) PCT Pub. No.: WO2017/074065
PCT Pub. Date: May 4, 2017

(65) Prior Publication Data
US 2018/0312889 A1    Nov. 1, 2018

(30) Foreign Application Priority Data

Oct. 27, 2015   (KR) .................. 10-2015-0149252
Oct. 27, 2016   (KR) .................. 10-2016-0141018

(51) Int. Cl.
*C12P 13/00*   (2006.01)
*C12N 15/70*   (2006.01)
(Continued)

(52) U.S. Cl.
CPC .......... *C12P 13/001* (2013.01); *C12N 9/1096* (2013.01); *C12N 15/70* (2013.01);
(Continued)

(58) Field of Classification Search
None
See application file for complete search history.

(56) References Cited

U.S. PATENT DOCUMENTS 8,530,206 B2    9/2013  Develter et al.
9,012,227 B2    4/2015  Karau et al.
(Continued)

FOREIGN PATENT DOCUMENTS

EP    3378941 B1    12/2019
JP    2009-096796 A   5/2009
(Continued)

OTHER PUBLICATIONS

Int'l Search Report from Int'l Appl'n No. PCT/KR2016/012174, dated Jan. 17, 2017.
(Continued)

*Primary Examiner* — Rebecca E Prouty
(74) *Attorney, Agent, or Firm* — Merchant & Gould P.C.

(57) ABSTRACT

The present invention relates to a method for producing a medium chain diamine and, more specifically, to a method for producing a medium chain diamine from an alcohol or alkane derived from a fatty acid, by culturing a recombinant microorganism from which a fatty aldehyde dehydrogenase gene in a ω-oxidative metabolic pathway and a β-oxidative metabolic pathway related gene have been deleted, and also into which a ω-transaminase gene has been introduced. The
(Continued)

recombinant microorganism disclosed in the present invention can prevent the additional oxidation and β-oxidation metabolism of fatty aldehyde and can produce a medium chain diamine with a high yield by introducing an amine group to the terminus thereof.

6 Claims, 9 Drawing Sheets

Specification includes a Sequence Listing.

(51) Int. Cl.
*C12N 15/81* (2006.01)
*C12N 9/10* (2006.01)

(52) U.S. Cl.
CPC ...... *C12N 15/81* (2013.01); *C12Y 102/01003* (2013.01); *C12Y 103/03006* (2013.01); *C12Y 206/01002* (2013.01)

(56) References Cited

U.S. PATENT DOCUMENTS

| | | |
|---|---|---|
| 2010/0317069 A1 | 12/2010 | Burk et al. |
| 2012/0282661 A1 | 11/2012 | Burk et al. |
| 2013/0303723 A1 | 11/2013 | Burk et al. |
| 2016/0304913 A1 | 10/2016 | Gatter et al. |
| 2017/0218414 A1 | 8/2017 | Burk et al. |

FOREIGN PATENT DOCUMENTS

| | | |
|---|---|---|
| KR | 10-1903552 B1 | 12/2011 |
| KR | 10-2012-0034640 A | 4/2012 |
| KR | 10-1145405 B1 | 5/2012 |

OTHER PUBLICATIONS

Written Opinion from Int'l Appl'n No. PCT/KR2016/012174, dated Jan. 17, 2017.

Rutter et al., "Engineering Yarrowia lipolytica for production of medium-chain fatty acids", Applied Microbiology and Biotechnology, vol. 99, pp. 7359-7368 (Electronic publishing Jul. 1, 2015).

Extended European Search Report from European Application No. 16860248.0, dated Sep. 20, 2018.

Zhi-Gang Qian et al., "Metabolic engineering of *Escherichia coli* for the production of cadaverine: A five carbon diamine", Biotechnology and Bioengineering, vol. 108, No. 1, pp. 93-103 (Jan. 30, 2011).

Dou et al., "Pheromone gland transcriptome of the pink bollworm moth, Pectinophora gossypiella: Comparison between a laboratory and field population," PLOS One, 19 pages (Jul. 22, 2019).

Lee et al., "Biotransformation of dicarboxylic acids from vegetable oil-derived sources: current methods and suggestions for improvement", Applied Microbiology and Biotechnology, 103:1545-1555 (2019).

Kemp et al., "Light sensitivity of the n-alkane-induced fatty alcohol oxidase from Candida tropicalis and Yarrowia ipolytica", Appl Microbiol Biotechnol, 32:461-464 (1990).

Kamasawa et al., "Immunoelectron Microscopic Observation of the Bahaviors of Peroxisomal Enzymes INducibly Synthesized in an n-Alkane-Utilizable Yeast Cell, Candida tropicalis", Cell Structure and Function, 21: 117-122 (1996).

| Genotype (with Phenotype) | ACO1 | ACO2 | ACO3 | ACO4 | ACO5 | ACO6 | FALDH1 | FALDH2 | FALDH3 | FALDH4 | cell stock No. |
|---|---|---|---|---|---|---|---|---|---|---|---|
| MatA leu2-270 ura3-302::Δleu2 | | | | | | | | | | | WT |
| MatA leu2-270 ura3-302::Δaco3Δura3Δku70Δaco5Δaco4Δaco6Δaco1Δaco2::LEU2 | x | x | x | x | x | x | | | | | Y1-11 |
| MatA leu2-270 ura3-302::Δaco1-6Δura3Δku70Δfaldh1-2Δω-transaminase(ALK1promoter) URA | x | x | x | x | x | x | x | | | ω-transaminase | Y2-20 |
| MatA leu2-270 ura3-302::Δaco1-6Δura3Δku70Δfaldh1-2Δω-transaminase(Exp1promoter) URA | x | x | x | x | x | x | x | x | | ω-transaminase | Y2-25 |
| MatA leu2-270 ura3-302::Δaco1-6Δura3Δku70Δfaldh1-2Δω-transaminase(TEFpromoter) URA | x | x | x | x | x | x | x | x | | ω-transaminase | Y2-30 |
| MatA leu2-270 ura3-302::Δaco1-6Δura3Δku70Δfaldh1-4Δω-transaminase(ALK1promoter) URA | x | x | x | x | x | x | x | x | x | ω-transaminase | Y2-35 |
| MatA leu2-270 ura3-302::Δaco1-6Δura3Δku70Δfaldh1-4Δω-transaminase(Exp1promoter) URA | x | x | x | x | x | x | x | x | x | ω-transaminase | Y2-36 |
| MatA leu2-270 ura3-302::Δaco1-6Δura3Δku70Δfaldh1-4Δω-transaminase(TEFpromoter) URA | x | x | x | x | x | x | x | x | x | ω-transaminase | Y3-1 |

FIG. 6

FIG. 9(a) Standard sample
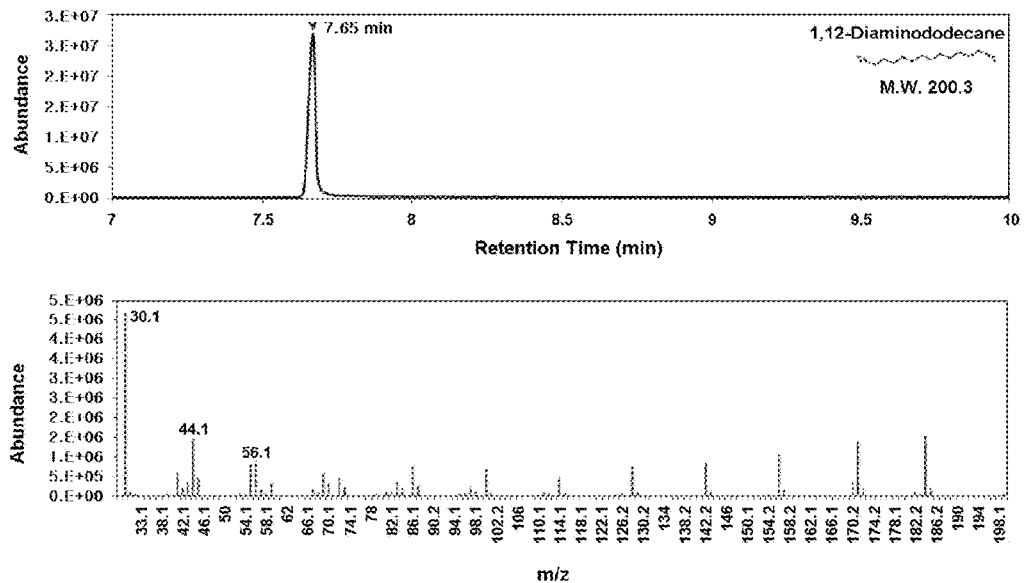
FIG. 9(b) Culture broth sample
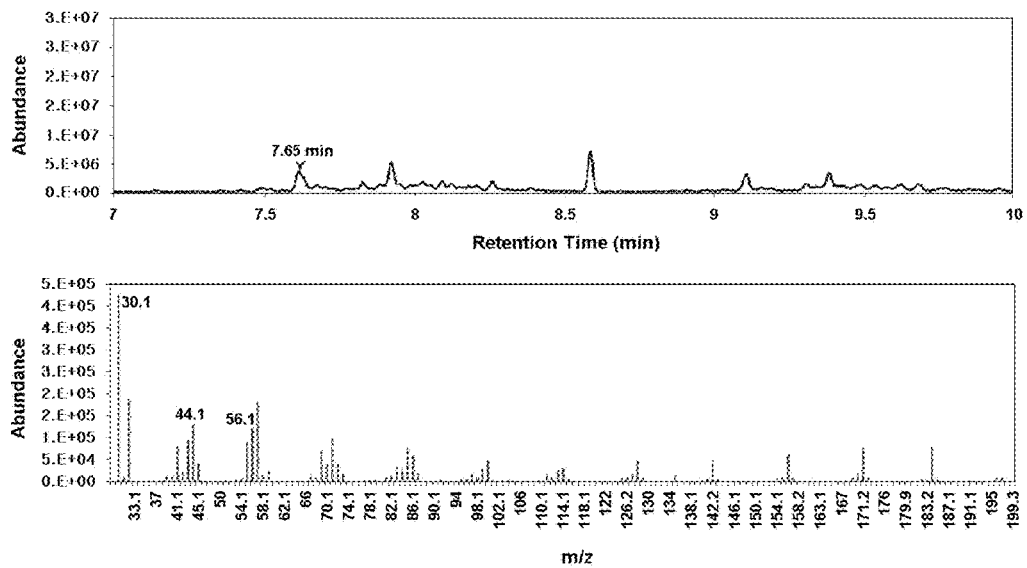

METHOD FOR PRODUCING MEDIUM CHAIN DIAMINE

This application is a National Stage Application of PCT/KR2016/012174, filed 27 Oct. 2016, which claims benefit of Serial No. 10-2016-0141018, filed 27 Oct. 2016 in Korea and Serial No. 10-2015-0149252, filed 27 Oct. 2015 in Korea and which applications are incorporated herein by reference. To the extent appropriate, a claim of priority is made to each of the above disclosed applications.

TECHNICAL FIELD

The present invention relates to a method for producing a medium chain diamine, and more particularly, to a method for producing a medium chain diamine from a fatty acid-derived alcohol or an alkane by culturing a recombinant microorganism from which a fatty aldehyde dehydrogenase (or fatty alcohol dehydrogenase) gene in an ω-oxidative metabolism pathway and β-oxidative metabolism pathway-related genes are deleted and into which an ω-transaminase gene is also introduced.

BACKGROUND ART

Bioplatform compounds are produced through biological or chemical conversion on the basis of biomass-derived raw materials, and thus have been used for synthesis of polymeric monomers, new materials, and the like.

Among the bioplatform compounds, a medium chain diamine is a material used as a monomer for polyamides. The polyamides are classified into aliphatic polyamides, aromatic polyamides, and aliphatic cyclic polyamides. Representative examples of the aliphatic polyamides include Nylon 6 and Nylon 66. In this case, the aliphatic polyamides are prepared through a condensation polymerization of adipic acid having 6 carbon atoms with hexamethylenediamine having 6 carbon atoms. Also, the aromatic polyamides have an aromatic framework introduced therein in order to further improve heat resistance, and are also known under the name of aramid.

Polyamides have received attention as engineering plastics capable of replacing metals such as polyacetal because they have excellent properties such as heat resistance, mechanical properties, electrical characteristics, and chemical resistance, and polyamide-based synthetic fibers mainly include synthetic fibers together with polyester-based/polyacrylonitrile-based fibers (i.e., acrylic fibers).

Production of medium chain diamines may be carried out using biological methods through chemical synthesis or microbial fermentation. In this case, the use of such biological methods requires the development of novel strains and the optimization of fermentation processes using metabolic engineering technology.

In the prior art, a microorganism which harbors both a β-oxidative metabolism pathway and an ω-oxidative metabolism pathway may be used as the strain capable of producing a medium chain diamine. For example, a method of producing hexamethylenediamine in a *Penicillium chrysogenum*-derived non-natural microbial organism is known (Korean Patent Unexamined Publication No. 10-2012-0034640). However, because the medium chain diamine is prepared by further introducing a process of transferring an amine group to a medium chain aldehyde corresponding to an intermediate product in an ω-oxidative metabolism pathway, the medium chain diamine has a drawback in that it may not be produced with high yield when it is produced using the microorganism.

DISCLOSURE

Technical Problem

Therefore, it is an object of the present invention to provide a method of producing a medium chain diamine from a fatty acid-derived alcohol or an alkane by culturing a recombinant microorganism from which a fatty aldehyde dehydrogenase gene in an ω-oxidative metabolism pathway and β-oxidative metabolism pathway-related genes are deleted and into which an ω-transaminase gene is also introduced.

Technical Solution

To solve the above problems, according to an aspect of the present invention, there is provided a method for producing a medium chain diamine, which comprises (1) preparing a recombinant microorganism from which a fatty aldehyde dehydrogenase gene in an ω-oxidative metabolism pathway and β-oxidative metabolism pathway-related genes are deleted and into which an ω-transaminase gene is also introduced; and (2) treating the recombinant microorganism with a substrate to culture the recombinant microorganism.

According to an embodiment of the present invention, the fatty aldehyde dehydrogenase gene and the β-oxidative metabolism pathway-related genes are preferably deleted from all homologous genes present in the microorganism, but the present invention is not limited thereto. According to another embodiment of the present invention, the fatty aldehyde dehydrogenase gene and the β-oxidative metabolism pathway-related genes are preferably deleted from some of the homologous genes present in the corresponding microorganism, but the present invention is not limited thereto.

According to an embodiment of the present invention, the fatty aldehyde dehydrogenase gene may be a gene selected from the group consisting of FALDH1, FALDH2, FALDH3, and FALDH4 genes, but the present invention is not limited thereto.

According to an embodiment of the present invention, the β-oxidative metabolism pathway-related genes may be an acyl-CoA oxidase gene, but the present invention is not limited thereto. According to preferred embodiments of the present invention, the acyl-CoA oxidase gene may be selected from the group consisting of ACO1, ACO2, ACO3, ACO4, ACO5, and ACO6 genes, but the present invention is not limited thereto.

According to an embodiment of the present invention, the microorganism may be a yeast or *Escherichia coli*, but the present invention is not limited thereto. According to preferred embodiments of the present invention, the yeast may be selected from the group of the yeast consisting of *Yarrowia* sp., *Saccharomyces* sp., *Pichia* sp., and *Candida* sp., but the present invention is not limited thereto. According to other preferred embodiments of the present invention, the *Yarrowia* sp. yeast may be *Yarrowia lipolytica*, but the present invention is not limited thereto.

According to an embodiment of the present invention, the substrate may be selected from the group consisting of a fatty acid-derived alcohol and an alkane, but the present invention is not limited thereto. According to preferred embodiments of the present invention, each of the fatty acid-derived alcohol, the alkane, and the medium chain diamine may have 5 to 30 carbon atoms, preferably 6 to 20 carbon atoms, and more preferably 8 to 16 carbon atoms, but the present invention is not limited thereto. According to other preferred embodiments of the present invention, the alkane may be dodecane, but the present invention is not limited thereto. According to other preferred embodiments of the present invention, the medium chain diamine may be 1,12-diaminododecane, but the present invention is not limited thereto.

Advantageous Effects

A recombinant microorganism disclosed in the present invention can produce a medium chain diamine with high yield by preventing additional oxidation and β-oxidation metabolism of fatty aldehydes and introducing an amine group to the terminus thereof because a fatty aldehyde dehydrogenase gene in an ω-oxidative metabolism pathway and β-oxidative metabolism pathway-related genes are deleted from the recombinant microorganism and an ω-transaminase gene is also introduced into the recombinant microorganism.

DESCRIPTION OF DRAWINGS

FIG. 6 is a graph illustrating types of transduced knock-out genes in the transformant microorganism according to the present invention.

FIG. 9(a) shows the GC/MS data showing that the medium chain diamine is produced from the dodecane substrate in the Y2-36 strain according to the present invention in a standard sample.

FIG. 9(b) shows the GC/MS data showing that the medium chain diamine is produced from the dodecane substrate in the Y2-36 strain according to the present invention in a culture broth sample.

BEST MODE

To achieve the objectives of the present invention, the present invention provides a method for producing a medium chain diamine, which includes:

(1) preparing a recombinant microorganism from which a fatty aldehyde dehydrogenase gene in an ω-oxidative metabolism pathway and β-oxidative metabolism pathway-related genes are deleted and into which an ω-transaminase gene is also introduced; and (2) treating the recombinant microorganism with a substrate to culture the recombinant microorganism.

Figure 1:
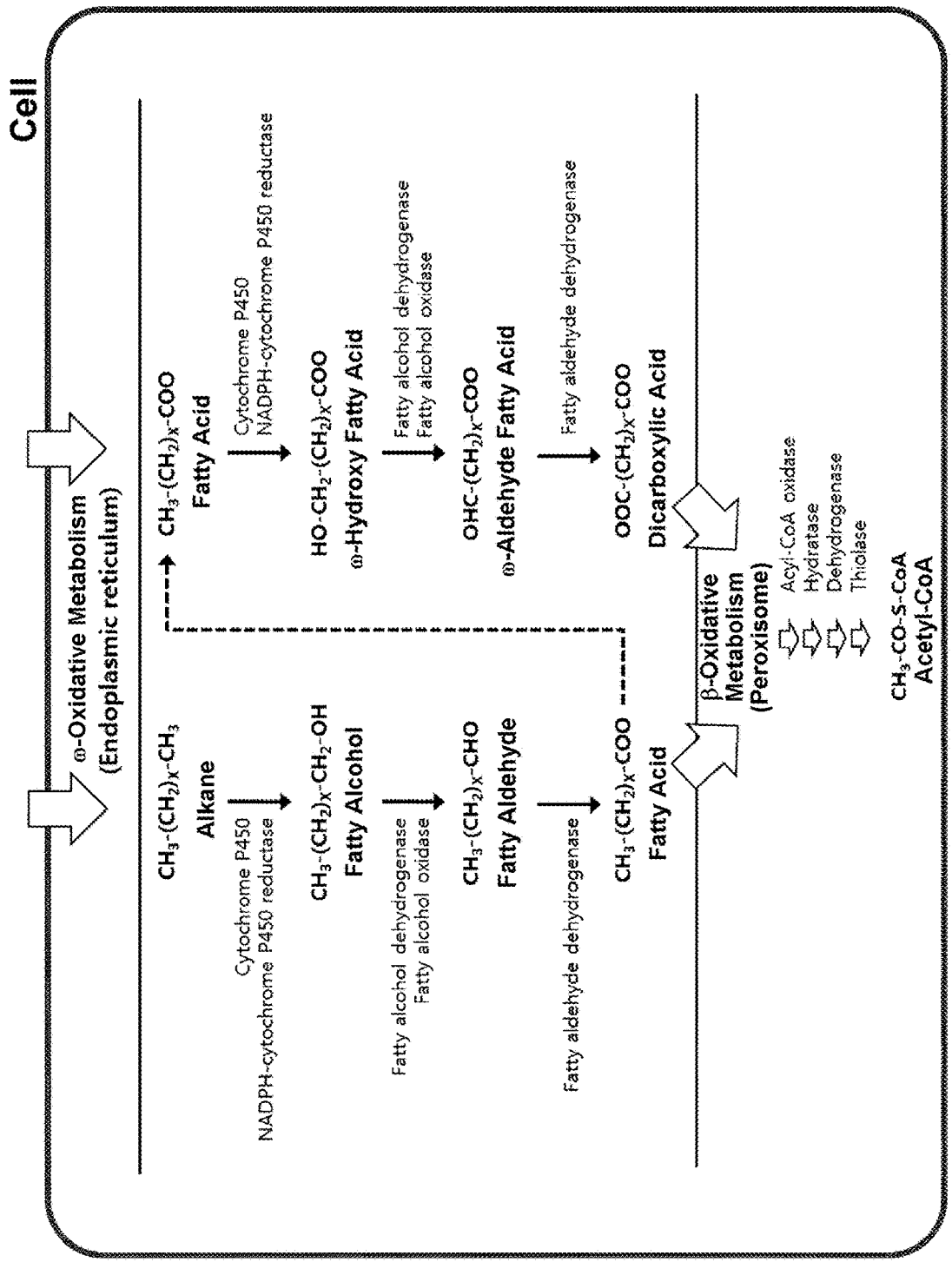
FIG. 1 is a diagram showing types of products and related enzymes associated with ω-oxidative and β-oxidative metabolism reactions.

In the present invention, the term "ω-oxidation" refers to a metabolic process in which the terminal methyl group of a fatty acid is oxidized to form dicarboxylic acid, and the term "β-oxidation" refers to a metabolic process in which a carbon atom at the β-position in a carboxyl group is oxidized to release acetyl-CoA, whereby fatty acids are gradually decomposed into fatty acids whose number of carbon atoms is reduced by two. The concept of the ω- and β-oxidations and the enzymes involved in such metabolic processes are widely known to persons having ordinary skill in the field of biochemistry. For example, when a fatty acid is used as the substrate for ω-oxidation, an ω-hydroxy fatty acid is first produced by means of an action of cytochrome P450 and an NADPH-cytochrome P450 reductase. Then, the ω-hydroxy fatty acid is converted into ω-aldehyde fatty acid by an action of a fatty alcohol dehydrogenase and a fatty alcohol oxidase, and the ω-aldehyde fatty acid is converted into dicarboxylic acid by an action of a fatty aldehyde dehydrogenase. Also, for the β-oxidation, a fatty acid whose number of carbon atoms is reduced by two is produced by an acyl-CoA oxidase (see FIG. 1).

Transaminase (TA, EC 2.6.1.X) is an enzyme which exists widely in nature and is involved in the transfer of an amine group in the nitrogen metabolism of an organism. Generally, transaminases serve to remove an amino group from one amino acid to transfer the amino group to another α-keto acid. The transaminases are used to produce optically pure non-natural amino acids and amine compounds because the transaminases have various outstanding advantages in that they exhibit wide specificity to substrates, high optical selectivity, a rapid reaction rate, and superior stability, and have no need for reproduction of coenzymes, and the like. The transaminases may be classified into five groups depending on the structures and multisequence alignments of proteins found in the Pfam database. Among these, the transaminases belonging to Group III including an ω-amino acid:pyruvate transaminase, an ornithine transaminase, a 4-aminobutyrate transaminase, and the like are referred to as ω-transaminases. Unlike the typical transaminases, the ω-transaminases perform a reaction of transferring an amine group of an amino acid- or carboxyl group-free amine compound, which contains an amine group at a position other than the α-position, to an amine receptor such as 2-ketoglutarate or pyruvate. Therefore, the ω-transaminases may be used as enzymes very useful for production of optically active amine compounds. For example, the ω-transaminases were first employed at 1990 by Celgene Co. (USA) to synthesize chiral amines. In recent years, the w-transaminases have been importantly employed for studies on asymmetric synthesis of chiral amines and studies on improvement of kinetic resolution. In 2012, Evonik Industries AG (Germany) reported one case in which 12-oxolauric acid methyl ester is converted into 12-aminolauric acid methyl ester using an ω-transaminase of a *Chromobacterium violaceum* DSM30191 strain.

According to an embodiment of the present invention, the fatty aldehyde dehydrogenase gene is preferably deleted from all homologous genes present in the corresponding microorganism, but a recombinant microorganism from which some of these genes are deleted may also be applied to the present invention, when necessary.

According to an embodiment of the present invention, the fatty aldehyde dehydrogenase gene may be selected from the group consisting of FALDH1, FALDH2, FALDH3, and FALDH4 genes, but the present invention is not limited thereto. The FALDH1, FALDH2, FALDH3, and FALDH4 genes may comprise base sequences set forth in SEQ ID NOs: 1 to 4, respectively, but the present invention is not limited thereto.

Figure 2:
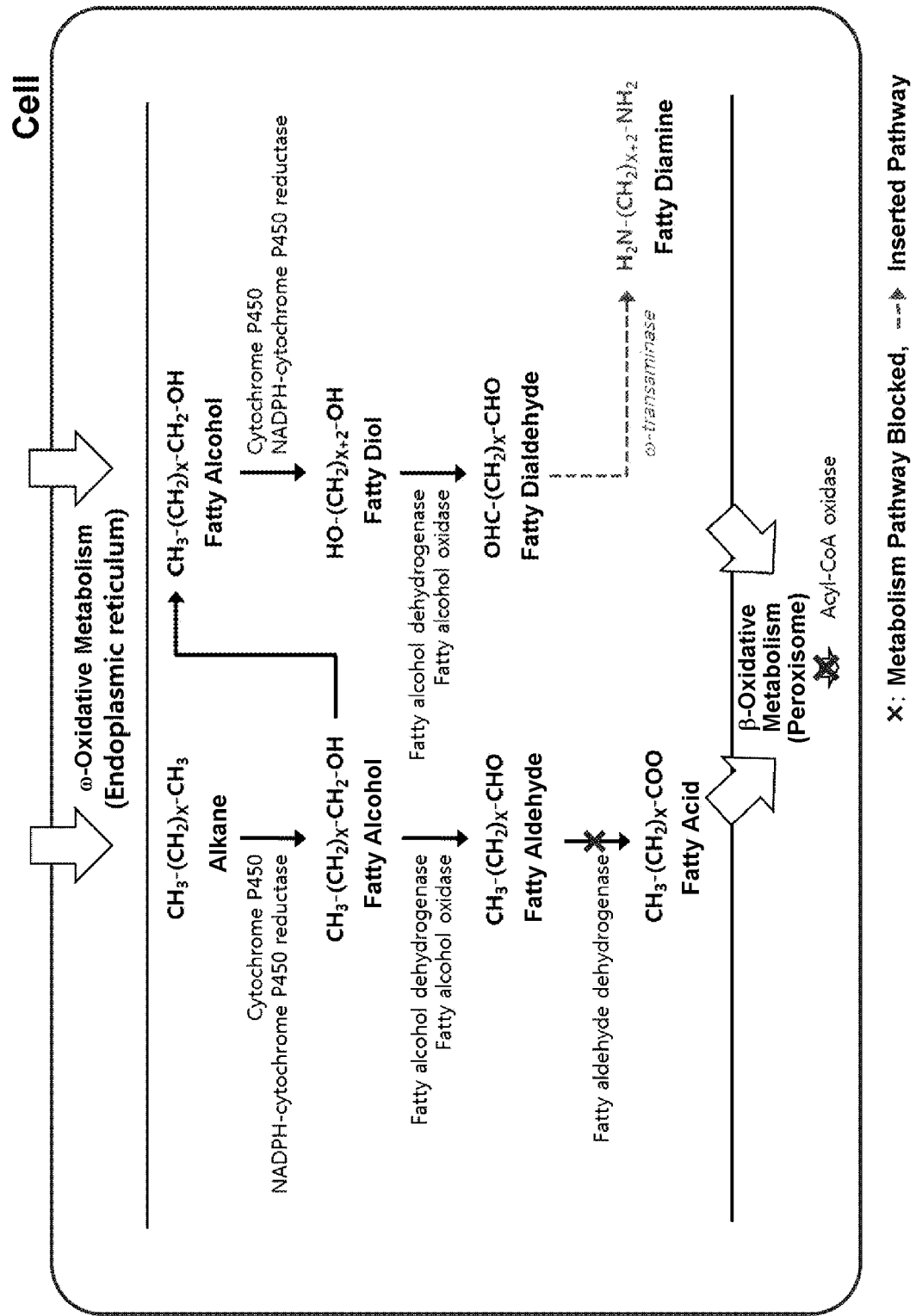
FIG. 2 is a diagram schematically showing a process of preparing a recombinant microorganism from which a fatty aldehyde dehydrogenase gene associated with ω-oxidation and β-oxidative metabolism pathway-related genes are deleted and into which an ω-transaminase gene is also introduced.

According to another embodiment of the present invention, the β-oxidative metabolism pathway-related genes are preferably deleted from all homologous genes present in the corresponding microorganism, but a recombinant microorganism from which some of these genes are deleted may also be applied to the present invention, when necessary. The β-oxidative metabolism pathway-related genes preferably includes an acyl-CoA oxidase gene, and the acyl-CoA oxidase gene may be selected from the group consisting of ACO1, ACO2, ACO3, ACO4, ACO5, and ACO6 genes, but the present invention is not limited thereto (see FIG. 2). According to other preferred embodiments of the present invention, the ACO1, ACO2, ACO3, ACO4, ACO5, and ACO6 genes may comprise base sequences set forth in SEQ ID NOs: 5 to 10, respectively, but the present invention is not limited thereto.

According to another embodiment of the present invention, the ω-transaminase gene may comprise a base sequence set forth in SEQ ID NO: 11, but the present invention is not limited thereto.

In the present invention, the recombinant microorganism from which the fatty aldehyde dehydrogenase gene and the β-oxidative metabolism pathway-related genes are deleted and into which the ω-transaminase gene is also introduced may be prepared using conventional geneticrecombinant technology known in the related art. In the present invention, the term "deletion" is used as a meaning generally encompassing a physical deletion of part or all of the corresponding gene, and also encompassing a situation in which a protein is not expressed from mRNA transcribed from the corresponding gene and a situation in which a protein expressed from the corresponding gene does not function. Also, the term "introduction" is used as a meaning generally encompassing all situations in which a gene is inserted into the genome of a microorganism, or a gene is expressed without insertion of the corresponding gene into the genome of the microorganism. Examples of the geneticrecombinant technology that may be used herein may include methods such as transformation, transduction, transfection, microinjection, electroporation, and the like, but the present invention is not limited thereto.

In the present invention, any microorganisms having both ω-oxidative and β-oxidative metabolism processes may be used without limitation. For example, eukaryotes including a yeast and prokaryotes including *Escherichia coli* may be used. According to an embodiment of the present invention, the yeast is preferably used as the microorganism. In this case, yeasts such as *Yarrowia* sp., *Saccharomyces* sp., *Pichia* sp., *Candida* sp., and the like may be used as the yeast without limitation. Among theses, *Yarrowia hpolytica*, *Candida tropicalis*, *Candida infanticola*, *Saccharomyces cerevisiae*, *Pichia alcoholophia*, or *Candida mycoderma* is preferably used. *Yarrowia hpolytica* is more preferably used.

As described above, in the case of the microorganism from which the fatty aldehyde dehydrogenase gene and the β-oxidative metabolism pathway-related genes are deleted and into which the ω-transaminase gene is also introduced, when an alkane is supplied as the substrate, one of both termini of the alkane is oxidized by an action of cytochrome P450 and an NADPH-cytochrome P450 reductase to form a primary alcohol. Then, a hydroxyl group of the alcohol is oxidized by an action of a fatty alcohol dehydrogenase and a fatty alcohol oxidase to form an aldehyde. However, because the fatty aldehyde dehydrogenase is deleted, no further oxidation occurs anymore. Also, the primary alcohol thus formed is again used as a substrate so that the other terminus of the primary alcohol is oxidized by an action of the cytochrome P450, the NADPH-cytochrome P450 reductase, the fatty alcohol dehydrogenase and the fatty alcohol oxidase to form aldehyde groups at both termini thereof. As described above, when the alkane is used as the substrate, the aldehyde is formed through a two-step oxidation reaction, whereas the aldehyde is formed through a one-step oxidation reaction when an alcohol other than the alkane is used as the substrate. The aldehyde groups thus formed at both of the termini of the primary alcohol are aminated by an action of an ω-transaminase to form a diamine.

In the present invention, the recombinant microorganism, from which the fatty aldehyde dehydrogenase gene in the ω-oxidative metabolism pathway and the β-oxidative metabolism pathway-related genes are deleted and into which the ω-transaminase gene is also introduced, may be used to produce a medium chain diamine by preventing additional oxidation and β-oxidative metabolism of fatty aldehydes and introducing an amine group into the terminus of the medium chain diamine. The fatty aldehyde dehydrogenase gene and the β-oxidative metabolism pathway-related genes are preferably deleted from all homologous genes present in the corresponding microorganism, but a recombinant microorganism from which some of these genes are deleted may also be applied to the present invention, when necessary.

In the present invention, any microorganisms having both ω-oxidative and β-oxidative metabolism processes may be used without limitation. For example, eukaryotes including a yeast and prokaryotes including *Escherichia coli* may be used. According to an embodiment of the present invention, the yeast is preferably used as the microorganism. In this case, yeasts such as *Yarrowia* sp., *Saccharomyces* sp., *Pichia* sp., *Candida* sp., and the like may be used as the yeast without limitation. Among theses, *Yarrowia lipolytica* Candida tropicalis, *Candida infanticola*, *Saccharomyces cerevisiae*, *Pichia alcoholophia*, or *Candida mycoderma* is preferably used. *Yarrowia lipolytica* is more preferably used.

In the present invention, the recombinant microorganism from which the fatty aldehyde dehydrogenase gene and the β-oxidative metabolism pathway-related genes are deleted and into which the ω-transaminase gene is also introduced may be prepared using conventional geneticrecombinant technology known in the related art. In the present invention, the term "deletion" is used as a meaning generally encompassing a physical deletion of part or all of the corresponding gene, and also encompassing a situation in which a protein is not expressed from mRNA transcribed from the corresponding gene and a situation in which a protein expressed from the corresponding gene does not function. Also, the term "introduction" is used as a meaning generally encompassing all situations in which a gene is inserted into the genome of a microorganism, or a gene is expressed without insertion of the corresponding gene into the genome of the microorganism.

In the present invention, the "diamine" generally refers to a compound that contains two amine groups (—NH$_2$ grouos), and the term "medium chain diamine" is used as a meaning encompassing all diamine compounds having 5 to 30 carbon atoms, preferably 8 to 16 carbon atoms. According to preferred embodiments of the present invention, the medium chain diamine is preferably 1,12-diaminododecane having 12 carbon atoms, but the present invention is not limited thereto.

In the present invention, the substrate of step (2) may be selected from the group consisting of a fatty acid-derived alcohol and an alkane, but the present invention is not limited thereto. According to an embodiment of the present invention, alcohols having 5 to 30 carbon atoms, preferably 8 to 16 carbon atoms may be used as the fatty acid-derived alcohol, but the present invention is not limited thereto. According to another embodiment of the present invention, alkanes having 5 to 30 carbon atoms, preferably 8 to 16 carbon atoms, and more preferably dodecane having 12 carbon atoms may be used as the alkane, but the present invention is not limited thereto.

Mode for Invention

Hereinafter, the present invention will be described in further detail with reference to examples thereof.

However, it should be understood that the following examples are just preferred examples for the purpose of illustration only and is not intended to limit or define the scope of the invention.

Example 1: Construction of Knock-Out Cassette

Figure 3:
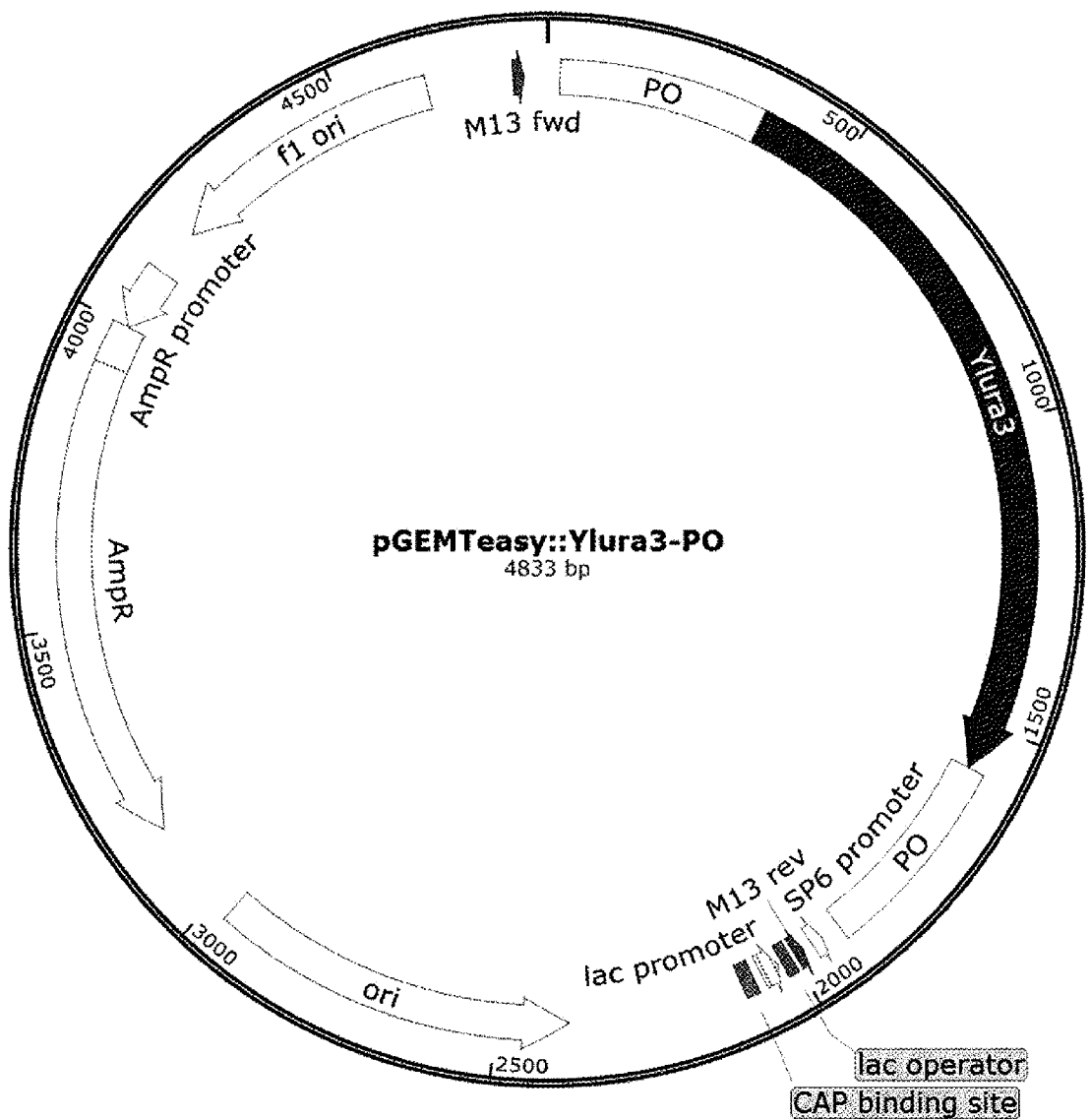
FIG. 3 is a diagram schematically showing a vector containing an ura3 gene to be used as a selective marker for gene knockout to modify a strain, and a pop-out region for deleting the ura3 gene after insertion of a knock-out cassette.

A vector containing an ura3 gene to be used as a selective marker for gene knockout to modify a strain, and a pop-out region for deleting the ura3 gene after insertion of a knock-out cassette was constructed (FIG. 3). A *Yarrowia*-derived gene was used as the ura3 gene, and the pop-out region used to modify a strain had a total of four sequences, and was referenced from two genes. Here, a *Bacillus*-derived glutamate-producing gene was used as one of the genes, and a gene associated with a *Salmonella*- or cloning vector pHUKH-derived His operon was used as the other one. The primers and sequences thereof used to construct the pop-out vectors are listed in the following Table 1.

TABLE 1

Pop-out Vectors

| Names | | Base Sequences | SEQ ID NOs |
|---|---|---|---|
| HisG1 | BglII F | aattgggcccagatctcagaccggttcagacaggat | 13 |
| | EcoRI R | tctctgggcggaattcggaggtgcggatatgaggta | 14 |
| | NotI F | tgTTTCTCGgcggccgccagaccggttcagacaggat | 15 |
| | BamHI R | TCCAACGCGTGGATCCggaggtgcggatatgaggta | 16 |
| HisG2 | BglII F | aattgggcccagatctaacgctacctcgaccagaaa | 17 |
| | EcoRI R | tctctgggcggaattctcttctcgatcggcagtacc | 18 |
| | NotI F | tgTTTCTCGgcggccgcaacgctacctcgaccagaaa | 19 |
| | BamHI R | TCCAACGCGTGGATCCtcttctcgatcggcagtacc | 20 |
| glt2 | BglII F | aattgggcccagatctTCAGAACTTGCGCCGATAAA | 21 |
| | EcoRI R | tctctgggcggaattcCTTTGCCAGCTAGACCATAGAG | 22 |
| | NotI F | tgTTTCTCGgcggccgcTCAGAACTTGCGCCGATAAA | 23 |
| | BamHI R | TCCAACGCGTGGATCCCTTTGCCAGCTAGACCATAGAG | 24 |
| glt3 | BglII F | aattgggcccagatctATTGGCGGGTTCGTTACTT | 25 |
| | EcoRI R | tctctgggcggaattcCCTGGAAGAAGGCCGTATTATC | 26 |
| | NotI F | tgTTTCTCGgcggccgcATTGGCGGGTTCGTTACTT | 27 |
| | BamHI R | TCCAACGCGTGGATCCCCTGGAAGAAGGCCGTATTATC | 28 |

Figure 4:
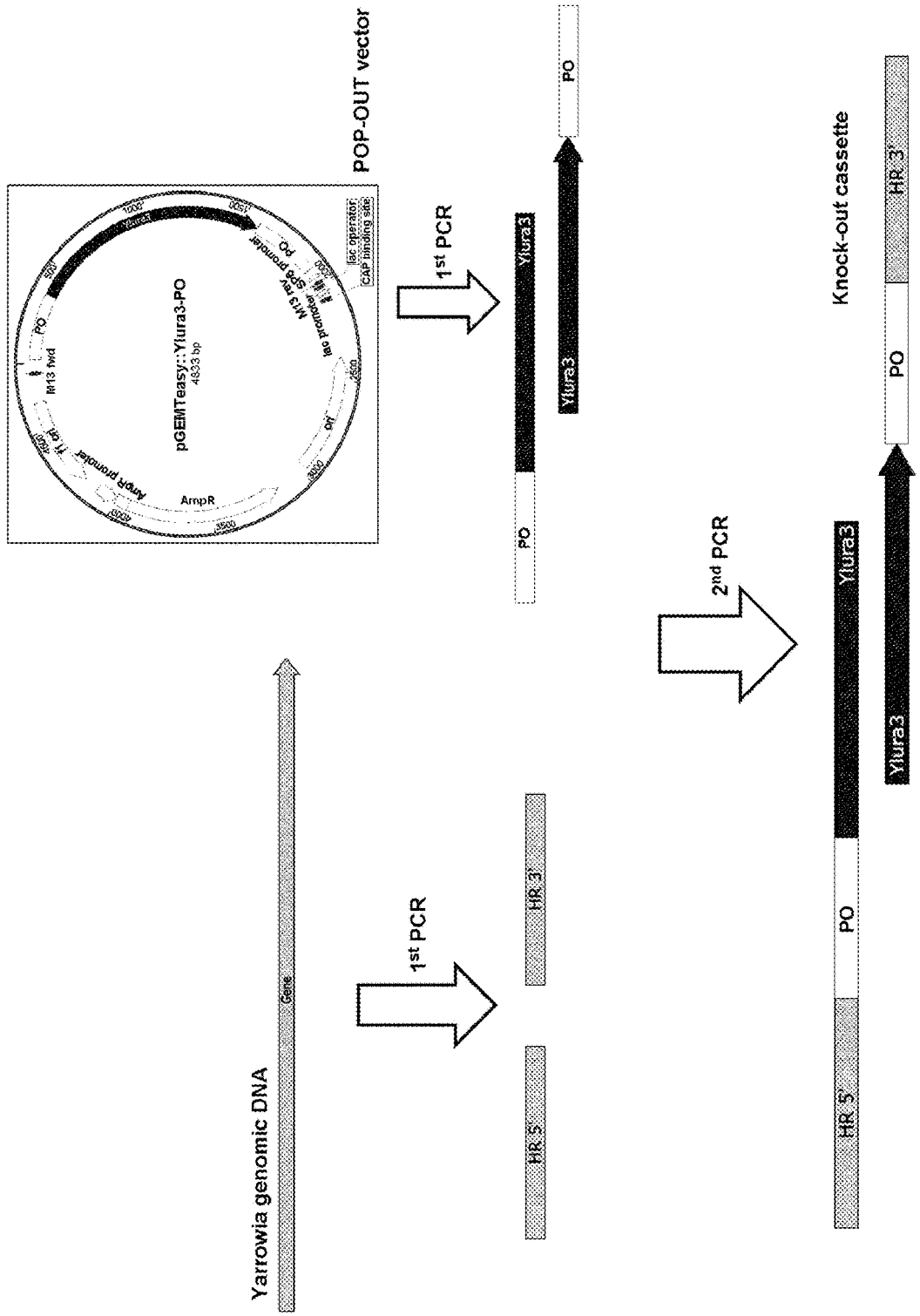
FIG. 4 is a schematic diagram showing a process of constructing a knock-out cassette used to prepare a transformant microorganism according to the present invention.

A knock-out cassette was constructed as shown in FIG. 4. First, PCR of a homologous region (HR) to be knocked out from the genomic DNA of *Yarrowia* sp., and PCR of two 5'- and 3'-terminal fragments from a pop-out vector were carried out separately. Thereafter, each of the 5' HR and 3' HR was subjected to alignment PCR ($2^{nd}$ PCR) with a PO-ura3 region to construct a knock-out cassette. The primers and sequences thereof used to amplify the respective homologous regions are listed in Table 2.

TABLE 2

Gene Deletions

| Names | | Base Sequences | SEQ ID NOs |
|---|---|---|---|
| ACO1 | F1 | TTCCTCAATGGTGGAGAAGA | 29 |
| | R1 | TCTTTATCCTGTCTGAACCGGTCTGGTACCATAGTCCTTGCCATGC | 30 |
| | F2 | ATCGCTACCTCATATCCGCACCTCCCTTCTGTCCCCCGAGTTTCT | 31 |

TABLE 2-continued

Gene Deletions

| Names | | Base Sequences | SEQ ID NOs |
|---|---|---|---|
| | R2 | AAGAAGGGCTTGAGAGTCG | 32 |
| ACO2 | F1 | CCCAACAACACTGGCAC | 33 |
| | R1 | TCTTTATCCTGTCTGAACCGGTCTG CTCCTCATCGTAGATGGC | 34 |
| | F2 | ATCGCTACCTCATATCCGCACCTCC gacaagacccgacaggc | 35 |
| | R2 | AGACCAGAGTCCTCTTCG | 36 |
| ACO3 | F1 | Accttcacagagccaccca | 37 |
| | R1 | ATGGCTCTCTGGGCGgtgttgggggtgttgatgatg | 38 |
| | F2 | TTGTTGTGTTTCTCGcaaggttctcatcgaggcctg | 39 |
| | R2 | Aggaaaggtcgaagagtgctct | 40 |
| ACO4 | F1 | Actgcgagagcgatctg | 41 |
| | R1 | TCTTTATCCTGTCTGAACCGGTCTG TTCATGAGCATGTAGTTTCG | 42 |
| | F2 | ATCGCTACCTCATATCCGCACCTCC gaggacgacaaagccggag | 43 |
| | R2 | AGAGCAGAGTCCTCCTCAA | 44 |
| ACO5 | F1 | AACTTCCTCACAGGCAGCGAGC | 45 |
| | R1 | ATGGCTCTCTGGGCG GAGTAGAGAGTGGGAGTTGAGGTC | 46 |
| | F2 | ttgttgtgtttctcg ccccgtcaaggacgctgag | 47 |
| | R2 | ACAGTAAGGTGGGGCTTGACTC | 48 |
| ACO6 | F1 | AGTCCCTCAACACGTTTACCG | 49 |
| | R1 | TCTTTATCCTGTCTGAACCGGTCTG CCATTTAGTGGCAGCAACGTT | 50 |
| | F2 | ATCGCTACCTCATATCCGCACCTCC GAGCTCGATCAACCGAACC | 51 |
| | R2 | AGGAAGGGTCTAATGACAGA | 52 |
| FALDH1 | F1 | AATCACTCCTCCTACGC | 53 |
| | R1 | TCTTTATCCTGTCTGAACCGGTCTG TGGTCTCGGGGACACCTC | 54 |
| | F2 | ATCGCTACCTCATATCCGCACCTCC CCATCATCAAGCCCCGAA | 55 |
| | R2 | ACCGACATAATCTGAGCAAT | 56 |
| FALDH2 | F1 | Accactaggtgagatcgag | 57 |
| | R1 | TCTTTATCCTGTCTGAACCGGTCTG CTCCGACACTACCGGAACGC | 58 |
| | F2 | ATCGCTACCTCATATCCGCACCTCC CTTGCTCCCACAGTTGTT | 59 |
| | R2 | GATCACCCAGAACCATAGC | 60 |
| FALDH3 | F1 | GTGACCCCCACCACGTCAC | 61 |
| | R1 | TCTTTATCCTGTCTGAACCGGTCTG TTCTGACATTTTCAGCGCCAC | 62 |
| | F2 | ATCGCTACCTCATATCCGCACCTCC CCATTACGAGCGTTTGACGG | 63 |
| | R2 | CAGGGCTGGGGACCACC | 64 |
| FALDH4 | F1 | TACCGACTGGACCAGATTC | 65 |
| | R1 | TCTTTATCCTGTCTGAACCGGTCTG CGGCAGTGGCAATGATCTTAC | 66 |
| | F2 | ATCGCTACCTCATATCCGCACCTCC GACTCGATTCATCGCTCCTAC | 67 |
| | R2 | CAAATCTTTCGGAAGATTCGG | 68 |

The primers used to PCR-amplify the pop-out region and ura3 as two fragments are listed in Table 3.

TABLE 3

Pop-out Cassettes

| Names | | Base Sequences | SEQ ID NOs |
|---|---|---|---|
| HISG1 | F | cagaccggttcagacaggat | 69 |
| | R | ggaggtgcggatatgaggta | 70 |
| HISG2 | F | aacgctacctcgaccagaaa | 71 |
| | R | tcttctcgatcggcagtacc | 72 |
| glt2 | F | TCAGAACTTGCGCCGATAAA | 73 |
| | R | CTTTGCCAGCTAGACCATAGAG | 74 |
| glt3 | F | ATTGGCGGGTTCGTTACTT | 75 |
| | R | CCTGGAAGAAGGCCGTATTATC | 76 |
| Bipartite cs 2B | Ulura3 | Atgccctcctacgaagctcgagc | 77 |
| | Ylura3F | Ctcccaacgagaagctggcc | 78 |

Example 2: Construction of Transduction Vector

Figure 5:
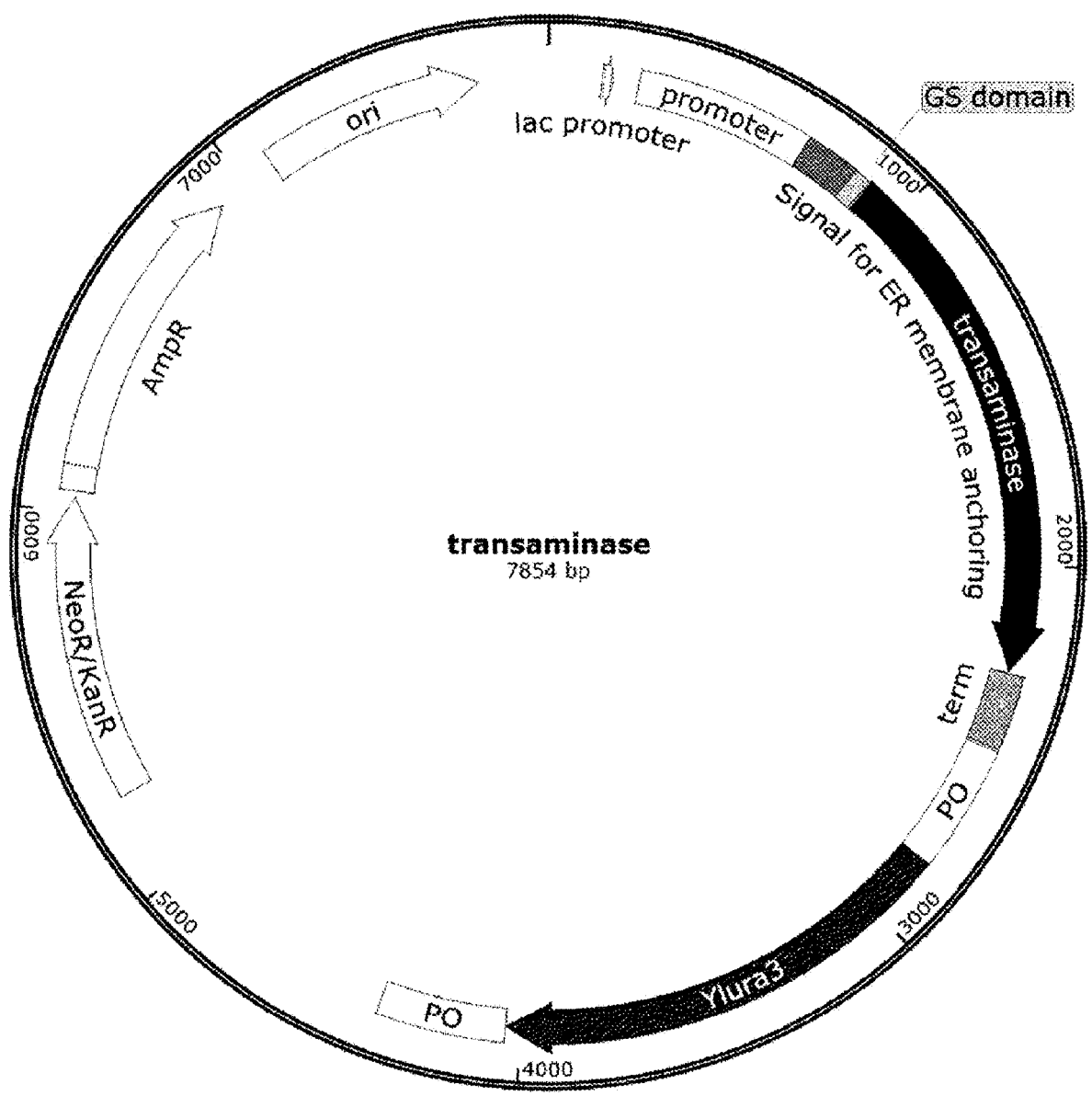
FIG. 5 is a diagram schematically showing a transformation vector containing an ω-transaminase gene for the purpose of modifying a strain.

To insert an ω-transaminase into a *Yarrowia* strain, a vector as shown in FIG. 5 was constructed. The primers used for this purpose are listed in Table 4.

TABLE 4

Transaminase Vectors

| Names | Base Sequences | SEQ ID NOs |
|---|---|---|
| EXP1-F | ccaagcttggtaccgagctcaGagtttggcgcccgttttttc | 79 |
| EXP1-R | CGTTGTTTTTGCATATGTGCTGTAGATATGTCTTGTGTGTAA | 80 |
| TEF-F | ccaagcttggtaccgagctcaaactttggcaaagaggctgca | 81 |
| TEF-R | CGTTGTTTTTGCATATGTTTGAATGATTCTTATACTCAGAAG | 82 |
| ALK1-F | ccaagcttggtaccgagctcagatctgtgcgcctctacagaccc | 83 |
| ALK1-R | CGTTGTTTTTGCATATGagtgcaggagtattctggggagga | 84 |
| XPR2t-F2 | gtcgacgcaattaacagatagtttgccg | 85 |

TABLE 4-continued

Transaminase Vectors

| Names | Base Sequences | SEQ ID NOs |
|---|---|---|
| XPR2t-R3 | ctcgagggatcccggaaaacaaaacacgacag | 86 |
| TA-F | CATATGCAAAAACAACGTACTACCTCCC | 87 |
| TA-R | gtcgacTTAGGCCAAACCACGGGCTTTC | 88 |
| ATATG2-ER-F | actcctgcactCATatgtccaacgccctcaacctg | 89 |
| XTATG2-ER-F | ccaatccaacacatatgtccaacgccctcaacctg | 90 |
| ER-R-1 | CGTTGTTTTTGCATAGAACCGCCACCGCCGCTACCG CCACCGCCCGAACCGCCACCGCCgaatcgtgaaatatccttgg gct | 91 |
| ER-R-2 | CGTTGTTTTTGCATatgAGAACCGCCACCGCCGCTAC CGCCACCGCCCGAACCGCCACCGCCgaatcgtgaaatatcct tgggct | 92 |
| ETATG2-ER-1 | tgattacgccaagcttGagtttggcgcccgttttttc | 93 |
| ETATG2-ER-2 | acaggttgagggcgttggacatATGTGCTGTAGATATGTCTTGT GTGTAA | 94 |
| TTATG2-ER-1 | tgattacgccaagcttaaactttggcaaagaggctg | 95 |
| TTATG2-ER-2 | acaggttgagggcgttggacatATGtttgaatgattcttatactcagaag | 96 |
| ER-F | atgtccaacgccctcaacctg | 97 |
| ER-R-3 | CGTTGTTTTTGCATAGAACCGCCACCGCCGCTAC | 98 |

The transaminase cassettes were constructed in the same manner as in FIG. 4, except that, when two fragments of PCR products were obtained from the vector, the genes spanning from a promoter to ura3 were amplified to construct the cassettes. The primers used to construct the cassettes are listed in the following Table 5.

TABLE 5

Transaminase Cassettes

| Names | Base Sequences | SEQ ID NOs |
|---|---|---|
| TA-FALDH4-F1 | TACCGACTGGACCAGATTC | 99 |
| TA-FALDH4-R1 | CGGCAGTGGCAATGATCTTAC | 100 |
| TA-FALDH4-F2 | ctcctctatggtctagctggcaaagACTCGATTCATCGCTCCTAC | 101 |
| TA-FALDH4-R2 | CAAATCTTTCGGAAGATTCGG | 102 |
| ATATG2-F | gtcggtaagatcattgccactgccgagatctgtgcgcctctacagac | 103 |
| ETATG2-F | gtcggtaagatcattgccactgccgGagtttggcgcccgttttttc | 104 |
| TTATG2-F | gtcggtaagatcattgccactgccgaaactttggcaaagaggctgc | 105 |
| XTATG2-F | gtcggtaagatcattgccactgccgacgcgtggagagtttgggtt | 106 |

The gene sequences used to modify the recombinant microorganism strain according to the present invention are listed in the sequence listing, and summarized in Table 6.

TABLE 6

| Genes | SEQ ID NOs |
|---|---|
| FALDH1 | 1 |
| FALDH2 | 2 |
| FALDH3 | 3 |
| FALDH4 | 4 |
| ACO1 | 5 |
| ACO2 | 6 |
| ACO3 | 7 |
| ACO4 | 8 |
| ACO5 | 9 |
| ACO6 | 10 |
| ω-transaminase | 11 |
| Ura3 | 12 |

Example 3: Preparation of Recombinant Microorganism Strain

The knock-out cassette constructed in Example 1 and the transduction vector constructed in Example 2 were used to prepare a total of eight knock-out strains from which some or all of a fatty aldehyde dehydrogenase gene in an ω-oxidative metabolism pathway present in a wild-type *Yarrowia* strain and β-oxidative metabolism pathway-related genes were deleted and into which an ω-transaminase gene was also introduced (FIG. 6). Specifically, a strain in which a gene was to be knocked out or be introduced was plated on an YPD plate, and cultured at 30° C. for 16 to 24 hours. The cultured cells were scraped with a loop, put into 100 μL of a one-step buffer (45% PEG4000, 100 mM DTT, 0.1 L of LiAc, 25 μg of single-strand carrier DNA), and vortexed. Thereafter, the knock-out cassette and the transduction vector (1 ng or more) were added thereto, and the resulting mixture was vortexed again, and then cultured at 39° C. for an hour. The cultured sample was loaded onto a selective medium (6.7 g/L of YNB without amino acids, and 20 g/L of glucose), and then cultured at 30° C. for 48 hours to screen the strains into which the constructed cassette was inserted. To check whether the cassettes were correctly inserted onto the genomes of the screened strains, PCR was then performed using the primers included in the gene deletions listed in Table 2.

To insert another cassette, a pop-out process was performed on the strain into which the cassette was inserted. The strain screened from the selective medium was inoculated in 2 mL of an YPD medium, and cultured at 30° C. for 16 hours, and 200 μL of the culture broth was then spread on a 5' FOA medium (6.7 g/L of YNB without amino acids, 20 g/L of glucose, 0.8 g/L of 5' FOA, 0.1 g/L of uracil, and 0.1 g/L of uridine), and then cultured at 30° C. for 48 hours. The strains grown on the 5' FOA medium were picked, and spread on an YPD plate and a UD plate to screen the strains grown on the YPD plate. Also, a PCR process was again performed using the primers listed in Table 2 to check whether the ura3 gene was deleted from the strains. A knock-out process was performed on other genes of the Ura3-free strains.

Example 4: Culturing of Recombinant Microorganism Strain

A day earlier, the strain to be cultured and tested was inoculated in 2 mL of an YPD medium (Bacto Laboratories, 10 g/L of Yeast extract, 20 g/L of peptone, and 20 g/L of glucose), and grown at 30° C. and 200 rpm for a day. 2 mL of a growth medium (pH 6.0) having the compositions listed in Table 7 was put into a 24-well plate, and a pre-cultured culture broth was inoculated at 1%. Thereafter, the strains were cultured at 30° C. and 450 rpm for a day in a plate stirrer. The strains cultured for a day were inoculated at a volume of 900 μL in a new plate containing 900 μL of a conversion medium (pH 7.6) listed in Table 8, and 200 μL of a substrate was added thereto at the same time. The resulting mixture was cultured at 30° C. and 450 rpm for a day. In this case, 10 g/L of dodecane dissolved in DMSO was used as the substrate.

TABLE 7

| Growth Medium (pH 6.0) | |
|---|---|
| Components | Concentration (g/L) |
| Glucose | 50 |
| YNB w/o amino acid | 6.7 |
| Yeast extract | 10 |
| (NH$_4$)$_2$SO$_4$ | 5 |
| Uracil | 0.05 |
| 0.1M phosphate buffer | |

| Preparation of 0.1M potassium phosphate buffer at 25° C. | | |
|---|---|---|
| pH | Volume (mL) of 1M K$_2$HPO$_4$ | Volume (mL) of 1M KH$_2$PO$_4$ |
| 6.0 | 13.2 | 86.8 |

TABLE 8

| Conversion Medium (pH 7.6) | |
|---|---|
| Components | Concentration (g/L) |
| Glucose | 30 |
| YNB w/o amino acid | 6.7 |
| Yeast extract | 3 |
| (NH$_4$)$_2$SO$_4$ | 15 |
| Uracil | 0.05 |
| L-alanine | 10 |
| 0.1M phosphate buffer | |

| Preparation of 0.1M potassium phosphate buffer at 25° C. | | |
|---|---|---|
| pH | Volume (mL) of 1M K$_2$HPO$_4$ | Volume (mL) of 1M KH$_2$PO$_4$ |
| 7.6 | 86.6 | 13.4 |

Figure 7:
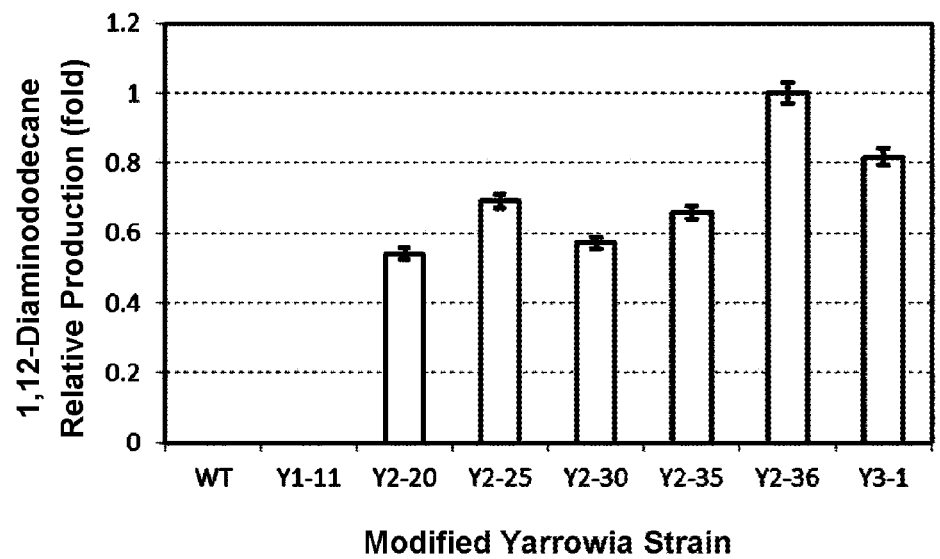
FIG. 7 is a graph illustrating an amount of a medium chain diamine produced from the dodecane substrate, using the transformant microorganism according to the present invention.
Figure 8:
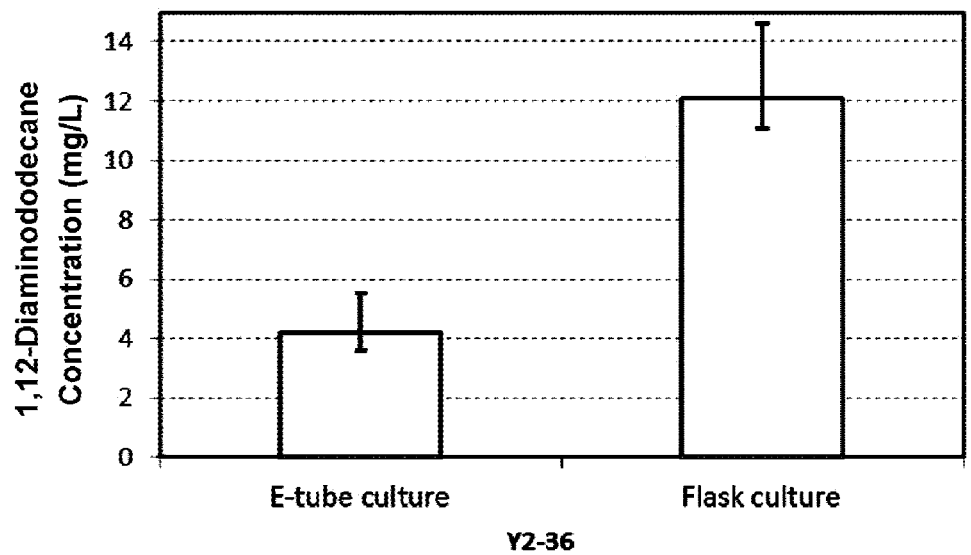
FIG. 8 is a graph illustrating an amount of the medium chain diamine produced from the dodecane substrate, when an Y2-36 strain of the present invention is cultured in a flask.

As a result, it was revealed that the Y1-11 strain in which only the β-oxidative metabolism pathway-related genes were knocked out did not produce 1,12-diaminododecane from dodecane serving as the substrate, but all the Y2-20, Y-2-25, Y2-30, Y2-35, Y2-36 and Y3-1 strains in which the fatty aldehyde dehydrogenase gene was further knocked out and into which the ω-transaminase was introduced exhibited an excellent ability to synthesize 1,12-diaminododecane (FIG. 7). Also, it was revealed that the Y2-36 strain exhibited an ability to synthesize approximately 12 mg/L of 1,12-diaminododecane when cultured in the flask (FIG. 8). In the following experiment, a sample analysis test was performed using the Y2-36 strain.

Example 5: Sample Analysis

300 μL of 6 N sulfuric acid was added to 1,000 μL of a culture broth of the Y2-36 strain, which had been proven to have the most excellent ability to synthesize 1,12-diaminododecane in Example 4, and then vortexed. Thereafter, the resulting mixture was centrifuged at 12,000 rpm for 2 minutes. Then, 200 μL of 10 N sodium hydroxide and 200 μL of diethyl ether were added to 600 μL of the supernatant, thoroughly vortexed, and then centrifuged at 12,000 rpm for 2 minutes. Then, a GC/MS assay was performed under the following analytical conditions to separate only a solvent layer.

Analytical Conditions

① Equipment: Agilent 5975 MSD
② Column: HP-5MS
③ Temperature: Oven (150° C. to 230° C.)
④ Carrier gas: He
⑤ Flow rate: 1 mL/min.

As a result, it was confirmed that the recombinant Y2-36 strain of the present invention was able to synthesize 1,12-diaminododecane from dodecane serving as a substrate (FIG. 9).

The invention claimed is:

1. A method for producing a medium chain diamine, comprising:
   (1) preparing a recombinant microorganism having both of ω-oxidative metabolism pathway and β-oxidative metabolism pathway of hydrocarbon from which fatty aldehyde dehydrogenase genes in the ω-oxidative metabolism pathway and the β-oxidative metabolism pathway-related genes are deleted and into which an ω-transaminase gene is also introduced;
   (2) treating the recombinant microorganism with a substrate to culture the recombinant microorganism,
   wherein the microorganism is *Yarrowia lipolytica*,
   the fatty aldehyde dehydrogenase genes are FALDH1, FALDH2, FALDH3, and FALDH4 genes and all of the ACO1, ACO2, ACO3, ACO4, ACO5, and ACO6 genes are deleted,
   the ω-transaminase gene comprises a base sequence set forth in SEQ ID NO: 11, and
   the β-oxidative metabolism pathway-related genes are acyl-CoA oxidase genes selected from the group consisting of ACO1, ACO2, ACO3, ACO4, ACO5, and ACO6 genes, and
   the substrate is selected from the group consisting of a fatty acid-derived alcohol and an alkane having 8 to 16 carbon atoms.

2. The method of claim 1, wherein each of the FALDH1, FALDH2, FALDH3, and FALDH4 genes comprises base sequences set forth in SEQ ID NOs: 1 to 4, respectively.

3. The method of claim 1, wherein each of the AC01, ACO2, ACO3, ACO4, ACO5, and ACO6 genes comprises base sequences set forth in SEQ ID NOs: 5 to 10, respectively.

4. The method of claim 1, wherein the alkane is dodecane.

5. The method of claim 1, wherein the medium chain diamine is a diamine compound having 8 to 16 carbon atoms.

6. The method of claim 5, wherein the medium chain diamine is 1,12-diaminododecane.

* * * * *

```
                          SEQUENCE LISTING

<160> NUMBER OF SEQ ID NOS: 106

<210> SEQ ID NO 1
<211> LENGTH: 1602
<212> TYPE: DNA
<213> ORGANISM: Yarrowia lipolytica
<220> FEATURE:
<221> NAME/KEY: gene
<222> LOCATION: (1)..(1602)
<223> OTHER INFORMATION: FALDH1 gene

<400> SEQUENCE: 1
atgtcctggg aaacaatcac tcctcctacg ccaatcgata cgtttgacag caacttgcaa      60
cgtcttcgag actctttcga gaccggcaag ctcgactctg tcgactaccg tctcgagcag     120
ctgcgaaccc tgtggttcaa gttctacgac aacctcgaca acatctacga ggcggtcacc     180
aaggatctcc atcgacccag gttcgaaacc gagctcaccg aggtactgtt tgttcgagac     240
gagttctcca ccgtcatcaa gaacctgcga aagtgggtca aggaagaaaa ggtggagaac     300
cccggaggcc ccttccagtt tgccaacccc cgaatccgac ccgttcctct gggagtggtg     360
ctggtcatca ctccctggaa ctaccccgtc atgctcaaca tctcacctgt gattgccgcc     420
attgctgccg gctgtcccat cgtgctcaag atgtccgagc tgtctcccca cacttccgct     480
gttcttggcc gaatcttcaa ggaggccctg gaccccggta tcatccaggt tgtttacgga     540 ggtgtcccg agaccaccgc ccttcttacc cagcattggg acaagatcat gtacaccgga     600
aacggagccg ttggtcgaat catcgcccag gccgcggtca gaacctgac tcctctagct     660 cttgagcttg gtggcaagtc acccgtgttc atcacttcca actgcaagag cgttatgacg     720
gccgctcggc gaatcgtgtg gggcaagttt gtcaacgccg ccagatctg tgtcgctcca     780 gactacattc tggttgctcc cgaaaaggag gccgagctcg tcgcttgtat caaggaggtg     840
ctccaagaac gatacggctc caagagagac gcccaccacc ccgatctgtc ccatatcatt     900
tccaagcccc attggaagcg tattcacaac atgatcgccc agaccaaggg agacatccag     960
gtgggtggac tcgagaacgc cgacgaagac caaaagttca tccagcccac aatcgtctcc    1020
aacgttccag atgacgacat tctcatgcag gacgagattt tcggacccat catcccatc    1080 atcaagcccc gaaccctcgg ccagcaggtt gattacgtca caagaaacca tgacaccccc    1140
ctggccatgt acatcttctc tgacgacccc aaggaggtgg actggctaca gacccgaatc    1200
cgagctggtt ctgtaaacat caacgaggtc attgagcagg tcggactggc ctctctgcct    1260
ctcagtggag ttggagcttc cggaaccgga gcataccatg gaaaattctc cttcgatgtc    1320
ttcacccaca gcaggccgt tatgggacag cccacctggc ccttctttga atacctcatg    1380
tattaccggt accctcctta ctccgagtac aagatgaagg tgctccgaac cctgttccca    1440
```

```
ccggttctga ttcctcgaac cggccgaccc gacgctactg ttcttcagcg agttctcggc   1500
aacaagctgc tttggatcat tattgccgcc cttgttgcgt acgccaaacg aaatgagctg   1560
ctcatcacca ttgctcagat tatgtcggtg tttattaagt ag                      1602

<210> SEQ ID NO 2
<211> LENGTH: 1566
<212> TYPE: DNA
<213> ORGANISM: Yarrowia lipolytica
<220> FEATURE:
<221> NAME/KEY: gene
<222> LOCATION: (1)..(1566)
<223> OTHER INFORMATION: FALDH2 gene

<400> SEQUENCE: 2
atgtcagagt tcgattggga gtcaattttg ccggcaacac cactaggtga gatcgagaag     60
gatattcaaa ccctacgaca gggcttcagg tccggaaaga cgctggattt gaacttcagg    120
cttgaccaga ttcgtaagct tttctatgct ctctatgata atgtcgatgc gatcaaagaa    180
gcaattcata aggatctcgg acgtccggtc ttcgagacta actttgcga gatctccttt     240 cagtggggtg aattcaataa tgtcgtttct aacttgaaga atgggcagc tgatgagacg     300 gtgaagggaa ccaccattca atacactctc acccggccaa agattagaaa gcgtccactt    360
ggtaccgtcc ttatcatatc tccttggaac tacccatttg ttctgaccat ctctcccctg    420
cttgctgctc tagcggcagg aaatacggtg gccctaaagt tctccgaaat gtgcccacat    480
acatcgcttt tgctgggaaa gttgtgcaca gaggcacttg ataaagaaat tttcaaggca    540 tttcaggag gcgttccggt agtgtcggag attctcaagt acaagttcga caaaatcatg    600
tacactggaa atcatcgagt tggcaagatc atcttggacg cagctaacaa ataccctcacc   660 cccgttattt tggagcttgg aggcaaatca ccagtcttcg tgactaagaa ttgccaaaac   720
gtatctcttg ctgccaagcg tgctctgtgg ggtaaactgg tcaacgctgg acaaacatgc   780
gttgcccccg attacatcat cgtcgagcct gaggtcgaac aggagtttat caaagcttgc    840
cagtactggg ttgagaagtt ctaccgaggt ggagttgact ctgatcataa ggacttcact    900
catattgcaa cacctggaca ttggagcga ttgacatcca tgcttgccca gacagaggga    960
aatatcatca caggcggaaa ttcggacgag aaatcacggt ttcttgctcc cacagttgtt  1020
gcgaaagttc ctgatggtga ttctttgatg aatgatgaga tctttggccc tatcctgccc  1080
atcctgacag ccagatccgt tgacgaaggt attcgctatg ttcatgagaa tcacgacact  1140
cccctggcca tgtatgtctt tactgataat gcatcagaag gagagtatat ccaatctcaa  1200
atcaactcag gtggcctgat attcaatgat agtcttgttc acgttggctg cgtgcaggcg  1260
ccttttggtg gtgtcggcca atccggctat ggtcttatc acggcgaaga ttccttcttg  1320 gcttttcac acaggcagac tttcatgaag cagccccatt tcatcgaacg accaatggcg  1380
atcagatatg cccctacac tagtcgaaaa caaaaggctg tccagggtag tctagctgct  1440 ccatctttc ctcgaacagg aaaggttgac cgctccctgt tggagcggat atttggtaag  1500
ctatggttct gggtgatcgt tttagggcta ggagcagcca gtttgaagtc aggaattttc  1560
ttatga                                                              1566

<210> SEQ ID NO 3
<211> LENGTH: 1590
<212> TYPE: DNA
<213> ORGANISM: Yarrowia lipolytica
<220> FEATURE:
<221> NAME/KEY: gene
```

```
<222> LOCATION: (1)..(1590)
<223> OTHER INFORMATION: FALDH3 gene

<400> SEQUENCE: 3
atgactacca ctgccacaga gaccccacg acaaacgtga ccccaccac gtcactgccc      60 aaggagaccg cctccccagg agggaccgct tctgtcaaca cgtcattcga ctgggagagc    120
atctgcggca agacgccgtt ggaggagatc gagtcggaca tttcgcgtct caaaaagacc    180
ttccgatcgg gcaaaactct ggatctggac taccgactcg accagatccg aaacctggcg    240
tatgcgatcc gcgataacga aaacaagatc cgcgacgcca tcaaggcgga cctgaaacga    300
cctgacttcg aaaccatggc ggccgagttc tcggtccaga tgggcgaatt caactacgtg    360
gtcaaaaacc tgccgaaatg ggtcaaggac gaaaaagtca agggaaccag catggcgtac    420
tggaactcgt cgccaaagat ccggaaacgg cccctgggct ccgtgcttgt catcacgccc    480
tggaactacc cactgattct ggccgtgtcg cctgttctgg gcgccattgc cgcaggcaac    540
accgtggcgc tgaaaatgtc agaaatgtca cccaacgcgt caaggtgat tggcgacatt     600 atgacagctg ccctggaccc ccagctcttt caatgcttct tcggaggagt ccccgaaacc    660
accgagatcc tcaaacacag atgggacaag atcatgtaca ccggaaacgg caaagtgggc    720
cgaatcatct gtgaggctgc caacaagtac ttgacacctg tggagctcga actcggagga    780
aagtcgcctg ttttcgtcac caaacactgc tccaacctgg aaatgccgc ccgccgaatc     840 atctggggca aattcgtcaa cggaggacaa acctgcgtgg ctccagacta cgttctggtg    900
tgtcccgagg tccacgacaa atttgtggct gcctgtcaaa aggtgctgga caagttctac    960
cctaacaact ctgccgagtc cgagatggcc catatcgcca cccctctcca ttacgagcgt   1020
ttgacgggcc tgctcaattc cacccgaggt aaggtcgttg ctggaggcac tttcaactcg   1080
gccacccggt tcattgctcc tacgattgtc gacgagtgg atgccaacga ttctctgatg    1140
cagggagaac tgtttggtcc tcttctcccc attgtcaagg ccatgagcac cgaggctgcc   1200
tgcaactttg tgcttgagca ccaccccacc ccctggcag agtacatctt tcagataac     1260 aattctgaga ttgattacat ccagatcga gtgtcgtctg gaggtctcgt gatcaacgac    1320
actctgatcc acgtgggatg cgtacaggcg cccttggag gtgtcggaga cagtggaaat     1380
ggaggatacc atggcaagca cactttcgat tgttcagcc attctcagac ggtcctcaga     1440
caacccggat gggtcgaaat gctgcagaag aaacggtatc ctccgtacaa caagagcaac   1500
gagaagtttg tccggagaat ggtggtcccc agccctggtt ttccccggga gggtgacgtg   1560
agaggatttt ggtcgagact cttcaactag                                    1590

<210> SEQ ID NO 4
<211> LENGTH: 1560
<212> TYPE: DNA
<213> ORGANISM: Yarrowia lipolytica
<220> FEATURE:
<221> NAME/KEY: gene
<222> LOCATION: (1)..(1560)
<223> OTHER INFORMATION: FALDH4 gene

<400> SEQUENCE: 4
atgtctacct tgattggga atccattgtg cctgccactc ctctcgacca gattcctggc     60
gacatccagc gactgcgaaa gggcttccga tccggaaaga ccctcgatct caactaccga   120
ctggaccaga ttcgaaactt gcactacgtc ctcagagaca atgtcgaggc catcaaggac   180
gccgtgtaca aggatctcgg ccgacccaag cacgagactg acctgtgcga ggtgggtttc   240
```

```
ctgtggggcg agtttaacaa cgtggttgcc aacctcaaga agtgggccgc cgacgaggac    300
gtcaagacca acctgcagta ctccatctcc tcccccaaga tccgaaagcg acctcttgga    360
aacgtgctca tcatctcgcc ctggaactac ccctttatgc tgaccgtgtc tcctctcatt    420
ggagctctgg ctgccggtaa cactgtggct gtcaagttct ccgaaatggc ccccacact     480 tccaaaattg ttggcgactt gtgcaccaag gccctcgacc ccgacgtctt ccaggccatc    540
cagggaggtg tccccgtcgt caccaagacc ctcgagcaga agttcgacaa gattatgtac    600
actggtaacc acactgtcgg taagatcatt gccactgccg ccaacaagta cctgacaccc    660
gtcatcctcg agctcggagg taagtcgccc gtttttgtca ccaagaactg caagaacatc    720
aagcttgccg ctaagcgagc cctgtggggt aaggtggtaa acgctggcca gacctgtgtg    780
gctcccgact acgtgattgt cgagcccgag gtggagcagg agtttatcga cgcctgcaag    840
tactggatta acgagttcta cagtggtaag attgaccagt acaaccccga ctttgccaag    900
atcgccaccc ccaaccactg gaaccgactt acctccatgt tgagcaagtc caagggagag    960
atcattactg gaggtaacac tgacgagaag actcgattca tcgctcctac tgtcgtcgca   1020
aaggtccccg acaatgattc cctgatggag gacgagattt tcggccctct tctgcccatt   1080
ctcactgccc gatccgtcga ggagggtatc aagtacgtgc acgagaacca cgacacccct   1140
cttgccatgt acgtcttcac tgacaaggcc tctgagggcg actacatcca gtcccagatc   1200
aactctggtg gccttatctt caatgacact ctgatccacg ttggatgtgt ccaggctccg   1260
tttggtggtg tcggcatgtc cggttacggt gcttaccatg gcgaggactc cttcctggcc   1320
ttcacccacc gacaaaccta cctcaaccag cccaagcttc tggagcctct tcaggacgtg   1380
cgatacgccc cctacaccaa aaccaagcga agcatggtca gaacctgct gctggtcggc    1440 cccattttcc cccgaaccgg ctccgtatac cccaacgtgc tgatccgaat cttccgaaag   1500
atttggttct gggtccttat tgtcgccatc ggagctgctg gtgccaaggc tctgctctag   1560
```

<210> SEQ ID NO 5
<211> LENGTH: 2034
<212> TYPE: DNA
<213> ORGANISM: Yarrowia lipolytica
<220> FEATURE:
<221> NAME/KEY: gene
<222> LOCATION: (1)..(2034)
<223> OTHER INFORMATION: ACO1 gene

<400> SEQUENCE: 5

```
atggccaagg agcgaggtaa gactcaattc actgtccgag atgtgaccaa cttcctcaat     60
ggtggagaag aagagaccca gattgtcgag aagatcatga gcagtattga acgtgatcca    120
gtactgtctg tcactgctga ctacgactgc aaccttcagc aggcccgaaa acagaccatg    180
gagcgggtgg ctgctctgtc gccttatctg gtcaccgata ctgagaagct atctctgtgg    240
cgtgcgcaac tgcatggaat ggttgatatg tctactcgta cgcggttgtc gatccacaac    300
aacctgttca ttggttccat caggggatct ggtactcctg aacagttcaa gtactgggtc    360
aagaagggag cggtggctgt taagcagttc tatggatgct ttgccatgac agagttgggc    420
catggaagca acctcaaggg actagagaca accgccactt atgaccagga cagtgaccag    480
ttcattatca acactcctca tattggtgct accaagtggt ggattggcgg tgcagcccac    540
acttccaccc attgtgtttg tttcgcgaaa ctgattgtgc atggcaagga ctatggtact    600
cgaaactttg tggtacctct ccgaaatgtc cacgatcaca gtctcaaggt cggtgtttca    660
attggagaca ttggaaagaa gatgggcaga gatggtgttg acaatggctg gatccagttc    720
```

```
accaatgttc gaatccccag acagaacatg ctaatgagat atgccaaggt gtctgatact    780
ggagtggtaa ccaaacccgc tcttgaccaa ctcacttatg gagccctcat tcgaggtcga    840
gtgtccatga ttgccgactc gttccacgtc tccaaacgat tcctcacaat tgctcttcgg    900
tacgcttgtg tccgacgaca gtttggaacc tctggagaca ctaaggagac caagatcatc    960 gactacccctt accaccagcg acgattgctg cctcttctgg cctactgcta cgctatgaag   1020
atgggtgctg atgaggctca gaagacttgg attgagacca ccgatcgaat tctggctctc   1080
aatcccaacg accccgccca gaagaacgat ctggagaagg ccgtcaccga cacaaaggag   1140
ctgtttgctg cgtctgcagg aatgaaggca tttaccacgt ggggatgtgc caaaatcatt   1200
gatgagtgcc gacaggcctg tggaggtcat ggatactctg gatataacgg atttggccag   1260
ggctacgctg actgggttgt ccagtgtacc tgggaaggag acaacaacgt tctgtgtctg   1320
tcaatgggcc gagggctggt tcagtcagct ctacagattt tggctggaaa gcacgtcggt   1380
gcttctattc agtacgtagg agacaagtct aaaatctccc agaacggcca gggtacccccc  1440 agagagcaac ttctgtcccc cgagtttcta gtagaagctt tcagaacggc ttctcgaaac   1500
aacattctca gaaccaccga taaataccaa gagcttgtca aaactctcaa tcccgaccag   1560
gcctttgagg agctgtctca gcagagattc cagtgtgctc gaatccacac acgacagcat   1620
cttatctctt cattctatgc ccgaattgcc actgccaaag acgatatcaa gccccatctg   1680
ctgaaactgg ccaatctgtt tgccctctgg tcaattgagg aggacactgg aatcttcctg   1740
cgggagaaca tcctcacccc tggagacatt gacctgatca acagtcttgt ggacgagctc   1800
tgtgttgcag ttcgagatca ggtaattgga ctcactgatg cctttggtct ctctgacttc   1860
ttcattaacg ctcccatcgg ctcctacgat ggtaatgttt acgaaaagta ctttgccaag   1920
gtcaaccagc aaaaccccgc tactaaccct cgtcctccct actacgagtc gactctcaag   1980
cccttcttgt tccgagaaga ggaggacgat gaaatttgcg atctcgatga gtga         2034
```

<210> SEQ ID NO 6
<211> LENGTH: 2103
<212> TYPE: DNA
<213> ORGANISM: Yarrowia lipolytica
<220> FEATURE:
<221> NAME/KEY: gene
<222> LOCATION: (1)..(2103)
<223> OTHER INFORMATION: ACO2 gene

<400> SEQUENCE: 6

```
atgaacccca caacactgg caccattgaa atcaacggta aggagtacaa caccttcacc      60 gagcccccg tggccatggc tcaggagcga gccaagacct ccttcccccgt gcgagagatg    120 acctacttcc tcgacggtgg cgagaagaac accctcaaaa acgagcagat catggaggag    180
attgagcgag accctctttt caacaacgac aactactacg atctcaacaa ggagcagatc    240
cgagagctca ccatggagcg agtcgccaag ctgtctctgt ttgtgcgtga tcagcccgag    300
gacgacatca agaagcgatt tgctctcatt ggtatcgccg atatgggaac ctacacccga    360
cttggtgtcc actacggcct cttctttggc gccgtccgag gtaccggaac tgccgagcag    420
tttggccact ggatctccaa gggagccgga gacctgcgaa agttctacgg atgtttctcc    480
atgaccgagc tgggccatgg ctccaacctg gctggtctcg agaccaccgc catctacgat    540
gaggagaccg acgagttcat catcaacacc cctcacattg ccgccaccaa gtggtggatt    600
ggaggagccg cccacaccgc cacccacact gtcgtgttcg cccgactcat tgtcaagggc    660
```

```
aaggactacg gtgtcaagac ctttgttgtc cagctgcgaa acatcaacga ccacagcctc    720
aaggtcggta tctctattgg tgatatcgga aagaagatgg gccgagacgg tatcgataac    780
ggatggatcc agttcaccaa cgtgcgaatc ccccgacaga acctgctcat gaagtacaca    840
aaggtcgacc gagagggtaa cgtgacccag cctcctctgg ctcagcttac ctacggttct    900
cttatcactg gtcgagtctc catggcctct gattctcacc aggtcggaaa gcgattcatc    960
accattgctc tgcgatacgc ctgcattcga cgacagttct ccaccacccc cggccagccc   1020
gagaccaaga tcatcgacta cccctaccat cagcgacgac ttctgcctct tctggcctat   1080
gtctatgctc ttaagatgac tgccgatgag gttggagctc tcttctcccg aaccatgctt   1140
aagatggacg acctcaagcc cgacgacaag gccggcctca atgaggttgt ttccgacgtc   1200
aaggagctct tctccgtctc cgccggtctc aaggccttct ccacctgggc ttgtgccgac   1260
gtcattgaca agacccgaca ggcttgcggt ggccacggtt actctggata caacggtttc   1320
ggccaggcct acgccgactg ggttgtccag tgcacctggg agggtgacaa caacattctc   1380
acccttcctg ccggccgagc tcttatccag tctgccgttg ctctgcgaaa gggcgagcct   1440
gttggtaacg ccgtttctta cctgaagcga tacaaggatc tggccaacgc taagctcaat   1500
ggccgatctc tcaccgaccc caaggtcctc gtcgaggcct gggaggttgc tgccggtaac   1560
atcatcaacc gagccaccga ccagtacgag aagctcattg gcgagggtct taacgccgac   1620
caggcctttg aggttctgtc tcagcagcga ttccaggccg ccaaggtcca cacgacga    1680 cacctcattg ccgctttctt ctcccgaatt gacaccgagg ctggcgaggc catcaagcag   1740
cccctgctta acctggctct gctgtttgcc ctgtggtcca tcgaagagga ctctggtctg   1800
ttcctgcgag agggcttcct cgagcccaag gatatcgaca ccgtcaccga gctcgtcaac   1860
aagtactgca ccactgtgcg agaggaggtc attggctaca ccgatgcctt caacctgtcc   1920
gactacttca tcaacgctcc tattggatgc tacgatggtg acgcttaccg acactacttc   1980
cagaaggtca acgagcagaa ccctgcccga gaccccgac ctccttacta cgcctctact   2040
ctcaagccct cctttttccg agaggaggag gatgatgaca tttgcgagct tgatgaggaa   2100
tag                                                                 2103
```

<210> SEQ ID NO 7
<211> LENGTH: 2103
<212> TYPE: DNA
<213> ORGANISM: Yarrowia lipolytica
<220> FEATURE:
<221> NAME/KEY: gene
<222> LOCATION: (1)..(2103)
<223> OTHER INFORMATION: ACO3 gene

<400> SEQUENCE: 7

```
atgatctccc ccaacctcac agctaacgtc gagattgacg gcaagcagta caacaccttc     60
acagagccac ccaaggcgct cgccggcgag cgagccaagg tcaagttccc catcaaggac    120
atgacggagt ttctgcacgg tggcgaggag aacgtgacca tgatcgagcg actgatgacg    180
gagctcgagc gagaccccgt gctcaacgtg tcggcgact acgacatgcc caaggagcag    240
ctgcgagaga cggccgtggc gcgaattgcg gcgctgtccg gccactggaa gaaggacaca    300
gaaaaggagg cgctgctgcg gtcccagctg cacggcattg tggacatggg caccccgaatc    360 cgactcggtg tgcacacggg cctgttcatg ggcgccatcc ggggttccgg caccaaggag    420
cagtacgact actgggtgcg aaagggcgcc gcggacgtca agggcttcta cggctgcttt    480
gctatgaccg agctgggcca tggctccaac gtggccggtc ttgagaccac cgccacctac    540
```

```
atccaggaca cggacgagtt catcatcaac accccccaaca ctggagccac caagtggtgg    600
attggaggag ccgcccactc ggccacccac accgcctgct tgctcgtcgt gcttgtcgac    660
ggcaaggact acggcgtcaa gatctttgtt gtccagctgc gagacgtctc ttctcactct    720
ctcatgcccg gcatcgctct cggcgacatt ggaaagaaga tgggccgaga cgccatcgac    780
aacggctgga tccagttcac caatgtgcga atccccgac agaacatgct catgaagtac    840
gccaaggtct cgtctaccgg caaggtgtcg cagcctcctc tggcccagct cacctacggc    900
gctctcattg gcggccgagt caccatgatt gccgactcct tctttgtctc ccagcgattc    960
atcaccattg ctctgcgata cgcctgtgtg cgacgacagt ttggcaccac cccggccag    1020 cccgagacta agatcatcga ctaccccctac catcagcgac gtctgctgcc tcttctggcc    1080
ttcacctacg ccatgaagat ggccgccgac cagtcccaga ttcagtacga tcagaccacc    1140
gatctgctgc agaccatcga ccctaaggac aagggcgctc tgggcaaggc cattgtcgac    1200
ctcaaggagc tgtttgcctc ttctgctggt ctcaaggcct tcaccacctg gacctgtgcc    1260
aacatcattg accagtgccg acaggcctgc ggtggccacg gctactctgg ctacaacggc    1320
tttggccagg cctacgccga ctgggttgtc cagtgcacct gggagggtga caacaacgtc    1380
ctgtgtctgt ccatgggccg aggtctcatc cagtcgtgtc tgggccaccg aaagggtaag    1440
cctctgggct cttctgtcgg ctacctggct aacaagggtc ttgagcaggc tactctgagc    1500
ggccgagacc tcaaggaccc caaggttctc atcgaggcct gggagaaggt cgccaacggc    1560
gccatccagc gggccactga caaatttgtc gagctcacca agggcggcct ctctcctgac    1620
caggcctttg aggagctgtc gcagcagcga ttccagtgtg ccaagatcca caccgaaag    1680 cacctggtga ctgccttcta cgagcgaatc aacgcctctg cgaaggccga cgtcaagcct    1740
tacctcatca acctcgccaa cctcttcact ctgtggtcca ttgaggagga ctctggtctc    1800
ttcctgcgag agggtttcct gcagcccaag gacattgacc aggtgactga gctggtgaac    1860
cactactgca aggaggttcg agaccaggtt gccggctaca ccgatgcctt tggtctgtct    1920
gactggttca tcaacgctcc cattggaaac tacgatggtg acgtttacaa gcattacttt    1980
gccaaggtta accagcagaa ccctgctcag aaccccccgac ctccttacta tgagagcact    2040
cttcgacctt tcctgttccg agaggatgag gatgacgaca tttgcgagct ggacgaggaa    2100
tag                                                                   2103
```

<210> SEQ ID NO 8
<211> LENGTH: 2106
<212> TYPE: DNA
<213> ORGANISM: Yarrowia lipolytica
<220> FEATURE:
<221> NAME/KEY: gene
<222> LOCATION: (1)..(2106)
<223> OTHER INFORMATION: ACO4 gene

<400> SEQUENCE: 8

```
atgatcaccc caaaccccgc taacgacatt gtccatgacg gcaagctcta cgacaccttc     60
actgagcccc ccaagctgat ggctcaggag cgagctcagc tggacttcga ccctagagac    120
atcacctact tctggatgg ctctaaggag gagaccgagc tgctggagtc gctcatgctc    180
atgtacgagc gagaccctct cttcaacaac cagaacgagt acgatgaatc gtttgaaaca    240
ctgcgagagc gatctgtgaa gcgaattttc cagctgtcca agtccatcgc catggacccc    300
gagcccatgt ctttccgaaa gattgggttc ctgggtattc ttgacatggg aacgtatgct    360
```

```
cgactgggag tccactacgc gctcttctgt aactccatcc ggggccaggg aaccccgat    420 cagctcatgt actggctgga ccagggagcc atggtcatca agggcttcta cggctgtttt    480
gccatgaccg aaatgggcca tggatctaac ctgtcgcgtc tggaaaccat cgccactttc    540
gacaaagaga ccgacgaatt tatcattaac acgccccacg ttggagccac aaagtggtgg    600
attggtggtg ctgctcacac tgctactcac acacttgcct ttgcccgtct tcaagtagac    660
ggaaaggact acggtgtgaa atcgtttgtc gtacctctcc gaaacctgga cgaccattcg    720
ctgcgtcctg gaatcgccac aggtgatatt ggtaagaaga tgggtcgaga tgccgttgac    780
aacggctgga ttcagttcac caacgtccga gtgccccgaa actacatgct catgaagcat    840
accaaggttc ttcgagacgg taccgtcaag cagccgcctt ggcccaact gacttacgga    900 tctctcatca ctggacgagt ccagatgacc actgactctc acaatgtgtc caaaaagttc    960
ctcaccattg ccctgagata cgccaccatc cgacgacagt tctcgtcaac tccaggagag   1020
cccgaaaccc gactaattga ctacctgtac caccaaagac gactcctgcc tcttatggct   1080
tactcttacg ccatgaaact agctggagat cacgtccgag agctgttctt tgcatcccag   1140
gagaaggctg agagcctcaa ggaggacgac aaagccggag ttgagtctta cgtccaggat   1200
atcaaggagc tcttctctgt ttctgctggt ctcaaggctg ccactacatg ggcttgtgct   1260
gacatcattg acaaggcccg acaggcgtgt ggaggccacg gatactctgc ctacaacggc   1320
tttggacagg ccttccagga ctgggttgtc cagtgcactt gggagggtga caatactgtt   1380
ctgactctat ctgccggccg agctctgatc caatctgctc tcgtctaccg aaaggagggc   1440
aaactaggta acgccacgaa gtacctctct cggtccaagg agcttgccaa cgccaagaga   1500
aacggacgat ccctggaaga ccccaagctg ctcgtggagg catgggaggc tgtctctgcc   1560
ggtgctatca acgctgctac tgacgcttac gaggagctct ccaagcaggg agtttctgtt   1620
gacgagtgct ttgagcaggt gtcccaggag cgattccagg ctgcccgaat ccacactcga   1680
cgagctctta tcgaggcctt ctactcacga atcgccactg ctgatgagaa ggtgaagcct   1740
catctgatcc ctctggccaa cctgtttgcc ctgtggtcca ttgaggagga ctctgctctg   1800
ttcctggctg agggctactt tgagcctgag gatatcattg aggtgacttc tcttgtcaac   1860
aagtactgcg gaattgttcg aaagaacgtt attggataca ccgatgcctt caacctgtcc   1920
gactacttca tcaacgctgc cattggacga tacgacggag acgtgtacaa gaactacttt   1980
gagaaggtca acagcagta ccctcctgag ggtggcaagc tcactactac gaggatgtc    2040 atgaagccct tcctgcatcg agagcgaatt cccgatgtcc ccatggagcc cgaggatatt   2100
cagtaa                                                             2106
```

<210> SEQ ID NO 9
<211> LENGTH: 2100
<212> TYPE: DNA
<213> ORGANISM: Yarrowia lipolytica
<220> FEATURE:
<221> NAME/KEY: gene
<222> LOCATION: (1)..(2100)
<223> OTHER INFORMATION: ACO5 gene

<400> SEQUENCE: 9

```
atgaacaaca accccaccaa cgtgatcctt ggaggcaagg agtacgacac cttcaccgag     60
cctccggccc agatggagct ggagcgagcc aagacacaat tcaaggtccg agacgtgacc    120
aacttcctca caggcagcga gcaggagaca ctgctgaccg agcgaatcat gcgggagatt    180
gagcgagatc ccgttctcaa cgtcgccggc gactacgacg ccgatcttcc caccaagcga    240
```

```
cgacaagctg ttgagcgaat cggggctctg gcccgatacc tgcccaagga ttccgagaag      300
gaggccattt tgcgaggcca gctgcatggt attgtggaca tgggtacccg aacccgaatc      360
gccgttcact acggtctgtt tatgggcgcc attcgtggct caggaaccaa ggagcagtac      420
gattactggg tcgccaaggg cgccgctact ctgcacaaat tctatggctg ctttgccatg      480
actgagctgg gtcacggatc taacgtggcc ggtctcgaga ccaccgccac ccttgataag      540
gacaccgacg agttcatcat caacaccccc aactcgggag ccacaaagtg gtggattgga      600
ggagctgccc actctgctac ccacacggct tgtcttgccc gactcattgt tgatggcaag      660
gactatggtg ttaagatctt cattgttcag ctgcgagacc tcaactccca ctctctactc      720
aacggtattg ccattggaga tatcggcaag aagatgggcc gagatgccat tgataatggt      780
tggatccagt tcacagacgt ccgaattccc gacagaaca tgctcatgcg atacgaccgg      840
gtgtctcgag acggcgaggt taccacctcc gagcttgccc agctcaccta cggagcactt      900
ctgtctggcc gagtgaccat gattgccgag tctcacctcc tgtctgctcg gttcctcacc      960
attgctcttc ggtacgcctg tatccgtcga cagttcggag ctgtgcctga caagcccgag     1020
actaagctca tcgactaccc ctaccaccaa cgacgtctgc tgcctcttct ggcctacacc     1080
tacgccatga agatgggcgc cgacgaggcc cagcagcagt acaactcctc ctttggcgct     1140
cttctcaagc tcaaccccgt caaggacgct gagaagtttg ctgtcgccac tgccgacctc     1200
aaggctctgt ttgcctcttc tgccggaatg aaggccttca ccacctgggc tgccgccaag     1260
atcattgacg agtgccgaca ggcctgtggt ggccatggct actccggcta caacggtttc     1320
ggtcaggctt acgccgactg ggtcgtccaa tgcacttggg agggtgacaa caacgtgctg     1380
tgtctgtcca tgggtcgatc gctcatccag tcgtgcattg ccatgagaaa gaagaagggc     1440
catgtcggca agtcggtcga gtacctgcag cgacgagacg agctgcagaa tgcccgagtt     1500
gacaacaagc ctctcactga ccctgctgtg ctcatcactg catgggagaa ggttgcctgc     1560
gaggccatca acagagccac tgactccttc atcaagctca cccaggaggg tctgtctcct     1620
gaccaggcct ttgaggagct gtctcaacag agatttgagt gtgcgcgaat ccacacccga     1680
aagcatctga tcacctcgtt ctacgctcga atctccaagg ccaaggcccg agtcaagccc     1740
caccttactg ttcttgccaa cctctttgcc gtctggtcca tcgaggagga ctctggtctc     1800
ttccttcggg agggctgctt cgagcctgcc gagatggacg agatcaccgc tctggtcgac     1860
gagctgtgct gcgaggctcg agagcaggtc attggattca ccgacgcctt caacctgtcc     1920
gacttcttca ttaacgcccc cattggccga ttcgacggag acgcctacaa gcactacatg     1980
gacgaggtca aggctgccaa caaccctcgt aacacccatg ctccttacta cgagaccaag     2040
ctgcgaccct tcctgttccg acccgatgag gacgaggaga tttgcgacct ggacgagtag     2100
```

<210> SEQ ID NO 10
<211> LENGTH: 2070
<212> TYPE: DNA
<213> ORGANISM: Yarrowia lipolytica
<220> FEATURE:
<221> NAME/KEY: gene
<222> LOCATION: (1)..(2070)
<223> OTHER INFORMATION: ACO6 gene

<400> SEQUENCE: 10

```
atgctctctc aacagtccct caacacgttt accgagcccc cggtcgaaat ggcccgggag       60
cgaaaccaga cttccttcaa cccgcgtctg ctgacgtact ttctggacgg aggcgaaaag      120
```

```
aacactctgc ttatggaccg actgatgcaa gagtacgagc gagaccctgt gtttcgaaac      180
gagggcgact acgatattac cgatgtggcc cagtcgcgag agctggcctt caagcgaatc      240
gccaagctca tcgagtatgt gcacaccgac gacgaggaga cgtatctgta ccgatgcatg      300
cttctgggcc aaatcgatat gggagccttt gcccggtacg ccatccacca cggagtctgg      360
ggcggtgcca ttcgaggtgc aggaacgcct gagcagtacg aattctgggt caagaaagga      420
tctctgtcgg ttaagaagtt ctatggatcc ttctccatga ccgagctggg ccacggcagt      480
aacttggtgg gtctggagac caccgccacc ctggacaaga acgcagacga gttcgtgatc      540
aacactccca acgttgctgc cactaaatgg tggatcggag gagccgccga taccgccact      600
cacacagctg tgtttgcacg tctcattgtc gacggagagg accacggtgt caagacgttt      660
gtggtgcagc tgcgagacgt ggagactcac aacctgatgc ctggtattgc tatcggagac      720
tgcggcaaga agatgggacg tcagggaacc gacaacggct ggatccagtt cacccatgtg      780
cgaattcccc gacagaacat gctcatgcga tactgtcacg tggacagcga cggaaatgtt      840
accgagccca tgatggctca gatggcctac ggagctcttc tggctggccg agtcggaatg      900
gccatggaca gttatttcac ctcgcgaaag ttccttacca ttgctcttcg atatgccacc      960
attcgacgag cttttgctgc cggaggaggt caggagacca agctgatcga ctacccttac     1020
caccagcgac gtctgctccc cctcatggcc cagacatatg ccatcaagtg caccgccgat     1080
aaggtcagag atcagttcgt caaggtcacc gacatgctcc taaacctcga tgtttctgac     1140
caagaggccg tgcccaaggc cattgccgag gctaaggagc tcttctctgt ttctgctggt     1200
gtcaaggcta ccacaacttg gcttgcgca cacaccattg accagtgcag acaggcgtgt      1260
ggaggccacg gatactctgc ttacaacggt tttggacgtg cttactccga ttgggtgatc     1320
cagtgcacct gggagggaga caataacatt ctgtgtctgt cagctggcag agctctggtc     1380
cagtctaacc gagctgtccg ggctggcaag cccattggag gtcctaccgc ctacctggct     1440
gctcccgctg gttcccccaa gctcgctggt cgaaacttgt acgaccccaa ggtcatgatt     1500
ggggcctggg agactgtttc ccgagctctg atcaaccgaa ccaccgatga gtttgaggtg     1560
ctggccaaga agggtctgtc tactgcccag gcctacgagg agctgtccca gcaacgattc     1620
ctgtgtactc gaatccacac ccgtctgtac atggtcaaga acttctacga gcgaattgcc     1680
gaggagggca ccgagttcac caaggagcct cttaccagac ttgccaacct gtacgccttc     1740
tggtccgtcg aagaggaggc tggaatcttc ctccgagagg gctacatcac tccccaggag     1800
ctcaagtaca tcagtgccga gatccgaaag cagctcttgg aggtgcgaaa ggacgtcatt     1860
ggctacaccg atgccttcaa cgtgcctgat ttttcctca actctgccat ggacgagct      1920 gacggagatg tctacaagaa ctacttcaag gtggtcaaca ctcagaaccc tccccaagac     1980
cctcgacctc cttattacga gtctgtcatt agacccttcc tgttccgaaa ggacgaggat     2040
gaggaaattt gctctcttga ggatgagtag                                      2070
```

<210> SEQ ID NO 11
<211> LENGTH: 1380
<212> TYPE: DNA
<213> ORGANISM: Chromobacterium violaceum DSM30191
<220> FEATURE:
<221> NAME/KEY: gene
<222> LOCATION: (1)..(1380)
<223> OTHER INFORMATION: transaminase gene

<400> SEQUENCE: 11

```
atgcaaaaac aacgtactac ctcccaatgg agagaattgg atgcagccca tcatttgcat       60
```

```
ccatttaccg acaccgcatc cttgaatcaa gctggcgcac gtgtgatgac ccgtggcgag    120
ggcgtttacc tgtgggattc tgagggtaac aaaatcattg atggtatggc cggtttgtgg    180
tgtgtgaacg tgggttatgg tcgtaaagac ttcgcagaag cagcccgtcg tcagatggaa    240
gaattgcctt tctacaacac tttcttcaaa actacccacc cagctgtggt cgagttgtct    300
tccttgttgg ccgaagttac cccagctggt ttcgaccgcg ttttctacac caattcgggc    360
tccgagtctg ttgacaccat gatccgtatg gtgcgccgtt attgggacgt ccagggcaag    420
cctgagaaga aaaccttgat tggccgctgg aatggttatc atggttccac cattggtggc    480
gcatcgttgg gcggtatgaa atacatgcac gaacagggcg atttgcctat cccaggtatg    540
gcccacattg agcagccttg gtggtataag cacggtaaag atatgacccc tgacgaattt    600
ggtgtggttg ccgcacgctg gttggaagaa aagatcttgg atcggtgc cgataaggtc    660 gcagcctttg ttggcgagcc aattcaaggt gcaggtggtg ttatcgtccc acctgcaacc    720
tactggccag agatcgagcg tatttgccgt aagtatgacg ttttgttggt cgccgatgaa    780
gtgatctgcg gcttcggtcg caccggtgag tggtttggtc accaacactt tggcttccag    840
cctgacttgt ttaccgccgc aaagggcttg tcttccggtt acttgcctat tggtgctgtt    900
tttgtgggta acgcgtcgc agaaggcttg attgccggtg gcgactttaa tcatggcttc    960
acctactccg gccatcctgt gtgcgcagca gtcgcacacg caaatgtcgc cgctttgcgc   1020
gacgaaggca ttgtacagcg cgttaaagac gatattggtc catacatgca gaagcgctgg   1080
cgtgaaacct tctctcgttt cgagcacgtc gatgatgtgc gtggcgttgg tatggttcaa   1140
gccttcactt tggtcaaaaa caaggcaaag cgtgagttgt ttcctgattt cggtgagatc   1200
ggtaccttgt gccgtgacat cttttttccgt aacaacttga ttatgcgtgc atgtggtgat   1260
cacatcgtgt ccgcaccacc tttggttatg acccgtgccg aagtggacga gatgttggca   1320
gtggcagagc gctgtttgga agagtttgag cagaccttga agcccgtggg tttggcctaa   1380
```

<210> SEQ ID NO 12
<211> LENGTH: 1205
<212> TYPE: DNA
<213> ORGANISM: Yarrowia lipolytica
<220> FEATURE:
<221> NAME/KEY: gene
<222> LOCATION: (1)..(1205)
<223> OTHER INFORMATION: Ura3 gene

<400> SEQUENCE: 12

```
cgcccagaga gccattgacg ttctttctaa tttggaccga tagccgtata gtccagtcta     60
tctataagtt caactaactc gtaactatta ccataacata tacttcactg ccccagataa    120
ggttccgata aaaagttctg cagactaaat ttatttcagt ctcctcttca ccaccaaaat    180
gccctcctac gaagctcgag ctaacgtcca caagtccgcc tttgccgctc gagtgctcaa    240
gctcgtggca gccaagaaaa ccaacctgtg tgcttctctg gatgttacca ccaccaagga    300
gctcattgag cttgccgata aggtcggacc ttatgtgtgc atgatcaaaa cccatatcga    360
catcattgac gacttcacct acgccggcac tgtgctcccc ctcaaggaac ttgctcttaa    420
gcacggtttc ttcctgttcg aggacagaaa gttcgcagat attggcaaca ctgtcaagca    480
ccagtaccgg tgtcaccgaa tcgccgagtg gtccgatatc accaacgccc acggtgtacc    540
cggaaccgga atcattgctg gcctgcgagc tggtgccgag gaaactgtct ctgaacagaa    600
gaaggaggac gtctctgact acgagaactc ccagtacaag gagttcctag tcccctctcc    660
```

-continued

```
caacgagaag ctggccagag gtctgctcat gctggccgag ctgtcttgca agggctctct      720
ggccactggc gagtactcca agcagaccat tgagcttgcc cgatccgacc ccgagtttgt      780
ggttggcttc attgcccaga accgacctaa gggcgactct gaggactggc ttattctgac      840 ccccgggggtg gtcttgacg acaagggaga cgctctcgga cagcagtacc gaactgttga     900
ggatgtcatg tctaccggaa cggatatcat aattgtcggc cgaggtctgt acggccagaa      960
ccgagatcct attgaggagg ccaagcgata ccagaaggct ggctgggagg cttaccagaa     1020
gattaactgt tagaggttag actatggata tgtaatttaa ctgtgtatat agagagcgtg     1080
caagtatgga gcgcttgttc agcttgtatg atggtcagac gacctgtctg atcgagtatg    1140
tatgatactg cacaacctgt gtatccgcat gatctgtcca atggggcatg ttgttgtgtt    1200
tctcg                                                                 1205
```

```
<210> SEQ ID NO 13
<211> LENGTH: 36
<212> TYPE: DNA
<213> ORGANISM: Artificial Sequence
<220> FEATURE:
<223> OTHER INFORMATION: BglII F primer for HisG1

<400> SEQUENCE: 13
aattgggccc agatctcaga ccggttcaga caggat                                36

<210> SEQ ID NO 14
<211> LENGTH: 36
<212> TYPE: DNA
<213> ORGANISM: Artificial Sequence
<220> FEATURE:
<223> OTHER INFORMATION: EcoRI R primer for HisG1

<400> SEQUENCE: 14
tctctgggcg gaattcggag gtgcggatat gaggta                                36

<210> SEQ ID NO 15
<211> LENGTH: 37
<212> TYPE: DNA
<213> ORGANISM: Artificial Sequence
<220> FEATURE:
<223> OTHER INFORMATION: NotI F primer for HisG1

<400> SEQUENCE: 15
tgtttctcgg cggccgccag accggttcag acaggat                               37

<210> SEQ ID NO 16
<211> LENGTH: 36
<212> TYPE: DNA
<213> ORGANISM: Artificial Sequence
<220> FEATURE:
<223> OTHER INFORMATION: BamHI R primer for HisG1

<400> SEQUENCE: 16
tccaacgcgt ggatccggag gtgcggatat gaggta                                36

<210> SEQ ID NO 17
<211> LENGTH: 36
<212> TYPE: DNA
<213> ORGANISM: Artificial Sequence
<220> FEATURE:
<223> OTHER INFORMATION: BglII F primer for HisG2

<400> SEQUENCE: 17
aattgggccc agatctaacg ctacctcgac cagaaa                                36
```

<210> SEQ ID NO 18
<211> LENGTH: 36
<212> TYPE: DNA
<213> ORGANISM: Artificial Sequence
<220> FEATURE:
<223> OTHER INFORMATION: EcoRI R primer for HisG2

<400> SEQUENCE: 18
tctctgggcg gaattctctt ctcgatcggc agtacc        36

<210> SEQ ID NO 19
<211> LENGTH: 37
<212> TYPE: DNA
<213> ORGANISM: Artificial Sequence
<220> FEATURE:
<223> OTHER INFORMATION: NotI F primer for HisG2

<400> SEQUENCE: 19
tgtttctcgg cggccgcaac gctacctcga ccagaaa       37

<210> SEQ ID NO 20
<211> LENGTH: 36
<212> TYPE: DNA
<213> ORGANISM: Artificial Sequence
<220> FEATURE:
<223> OTHER INFORMATION: BamHI R primer for HisG2

<400> SEQUENCE: 20
tccaacgcgt ggatcctctt ctcgatcggc agtacc        36

<210> SEQ ID NO 21
<211> LENGTH: 36
<212> TYPE: DNA
<213> ORGANISM: Artificial Sequence
<220> FEATURE:
<223> OTHER INFORMATION: BglII F primer for glt2

<400> SEQUENCE: 21
aattgggccc agatcttcag aacttgcgcc gataaa        36

<210> SEQ ID NO 22
<211> LENGTH: 38
<212> TYPE: DNA
<213> ORGANISM: Artificial Sequence
<220> FEATURE:
<223> OTHER INFORMATION: EcoRI R primer for glt2

<400> SEQUENCE: 22
tctctgggcg gaattccttt gccagctaga ccatagag      38

<210> SEQ ID NO 23
<211> LENGTH: 37
<212> TYPE: DNA
<213> ORGANISM: Artificial Sequence
<220> FEATURE:
<223> OTHER INFORMATION: NotI F primer for glt2

<400> SEQUENCE: 23
tgtttctcgg cggccgctca gaacttgcgc cgataaa       37

<210> SEQ ID NO 24
<211> LENGTH: 38
<212> TYPE: DNA
<213> ORGANISM: Artificial Sequence
<220> FEATURE:

```
<223> OTHER INFORMATION: BamHI R primer for glt2

<400> SEQUENCE: 24
tccaacgcgt ggatcccttt gccagctaga ccatagag                                38

<210> SEQ ID NO 25
<211> LENGTH: 35
<212> TYPE: DNA
<213> ORGANISM: Artificial Sequence
<220> FEATURE:
<223> OTHER INFORMATION: BglII F primer for glt3

<400> SEQUENCE: 25
aattgggccc agatctattg gcgggttcgt tactt                                   35

<210> SEQ ID NO 26
<211> LENGTH: 38
<212> TYPE: DNA
<213> ORGANISM: Artificial Sequence
<220> FEATURE:
<223> OTHER INFORMATION: EcoRI R primer for glt3

<400> SEQUENCE: 26
tctctgggcg gaattccctg gaagaaggcc gtattatc                                38

<210> SEQ ID NO 27
<211> LENGTH: 36
<212> TYPE: DNA
<213> ORGANISM: Artificial Sequence
<220> FEATURE:
<223> OTHER INFORMATION: NotI F primer for glt3

<400> SEQUENCE: 27
tgtttctcgg cggccgcatt ggcgggttcg ttactt                                  36

<210> SEQ ID NO 28
<211> LENGTH: 38
<212> TYPE: DNA
<213> ORGANISM: Artificial Sequence
<220> FEATURE:
<223> OTHER INFORMATION: BamHI R primer for glt3

<400> SEQUENCE: 28
tccaacgcgt ggatcccctg gaagaaggcc gtattatc                                38

<210> SEQ ID NO 29
<211> LENGTH: 20
<212> TYPE: DNA
<213> ORGANISM: Artificial Sequence
<220> FEATURE:
<223> OTHER INFORMATION: F1 primer for ACO1

<400> SEQUENCE: 29
ttcctcaatg gtggagaaga                                                    20

<210> SEQ ID NO 30
<211> LENGTH: 46
<212> TYPE: DNA
<213> ORGANISM: Artificial Sequence
<220> FEATURE:
<223> OTHER INFORMATION: R1 primer for ACO1

<400> SEQUENCE: 30
tctttatcct gtctgaaccg gtctggtacc atagtccttg ccatgc                       46
```

<210> SEQ ID NO 31
<211> LENGTH: 45
<212> TYPE: DNA
<213> ORGANISM: Artificial Sequence
<220> FEATURE:
<223> OTHER INFORMATION: F2 primer for ACO1

<400> SEQUENCE: 31
atcgctacct catatccgca cctcccttct gtcccccgag tttct          45

<210> SEQ ID NO 32
<211> LENGTH: 19
<212> TYPE: DNA
<213> ORGANISM: Artificial Sequence
<220> FEATURE:
<223> OTHER INFORMATION: R2 primer for ACO1

<400> SEQUENCE: 32
aagaagggct tgagagtcg          19

<210> SEQ ID NO 33
<211> LENGTH: 17
<212> TYPE: DNA
<213> ORGANISM: Artificial Sequence
<220> FEATURE:
<223> OTHER INFORMATION: F1 primer for ACO2

<400> SEQUENCE: 33
cccaacaaca ctggcac          17

<210> SEQ ID NO 34
<211> LENGTH: 43
<212> TYPE: DNA
<213> ORGANISM: Artificial Sequence
<220> FEATURE:
<223> OTHER INFORMATION: R1 primer for ACO2

<400> SEQUENCE: 34
tctttatcct gtctgaaccg gtctgctcct catcgtagat ggc          43

<210> SEQ ID NO 35
<211> LENGTH: 42
<212> TYPE: DNA
<213> ORGANISM: Artificial Sequence
<220> FEATURE:
<223> OTHER INFORMATION: F2 primer for ACO2

<400> SEQUENCE: 35
atcgctacct catatccgca cctccgacaa gacccgacag gc          42

<210> SEQ ID NO 36
<211> LENGTH: 18
<212> TYPE: DNA
<213> ORGANISM: Artificial Sequence
<220> FEATURE:
<223> OTHER INFORMATION: R2 primer for ACO2

<400> SEQUENCE: 36
agaccagagt cctcttcg          18

<210> SEQ ID NO 37
<211> LENGTH: 19
<212> TYPE: DNA
<213> ORGANISM: Artificial Sequence
<220> FEATURE:
<223> OTHER INFORMATION: F1 primer for ACO3

<400> SEQUENCE: 37
accttcacag agccaccca                                                19

<210> SEQ ID NO 38
<211> LENGTH: 36
<212> TYPE: DNA
<213> ORGANISM: Artificial Sequence
<220> FEATURE:
<223> OTHER INFORMATION: R1 primer for ACO3

<400> SEQUENCE: 38
atggctctct gggcggtgtt gggggtgttg atgatg                             36

<210> SEQ ID NO 39
<211> LENGTH: 36
<212> TYPE: DNA
<213> ORGANISM: Artificial Sequence
<220> FEATURE:
<223> OTHER INFORMATION: F2 primer for ACO3

<400> SEQUENCE: 39
ttgttgtgtt tctcgcaagg ttctcatcga ggcctg                             36

<210> SEQ ID NO 40
<211> LENGTH: 22
<212> TYPE: DNA
<213> ORGANISM: Artificial Sequence
<220> FEATURE:
<223> OTHER INFORMATION: R2 primer for ACO3

<400> SEQUENCE: 40
aggaaaggtc gaagagtgct ct                                            22

<210> SEQ ID NO 41
<211> LENGTH: 17
<212> TYPE: DNA
<213> ORGANISM: Artificial Sequence
<220> FEATURE:
<223> OTHER INFORMATION: F1 primer for ACO4

<400> SEQUENCE: 41
actgcgagag cgatctg                                                  17

<210> SEQ ID NO 42
<211> LENGTH: 45
<212> TYPE: DNA
<213> ORGANISM: Artificial Sequence
<220> FEATURE:
<223> OTHER INFORMATION: R1 primer for ACO4

<400> SEQUENCE: 42
tctttatcct gtctgaaccg gtctgttcat gagcatgtag tttcg                   45

<210> SEQ ID NO 43
<211> LENGTH: 44
<212> TYPE: DNA
<213> ORGANISM: Artificial Sequence
<220> FEATURE:
<223> OTHER INFORMATION: F2 primer for ACO4

<400> SEQUENCE: 43
atcgctacct catatccgca cctccgagga cgacaaagcc ggag                    44

<210> SEQ ID NO 44
<211> LENGTH: 19

<210> SEQ ID NO 44
<211> LENGTH: 19
<212> TYPE: DNA
<213> ORGANISM: Artificial Sequence
<220> FEATURE:
<223> OTHER INFORMATION: R2 primer for ACO4

<400> SEQUENCE: 44
agagcagagt cctcctcaa                                              19

<210> SEQ ID NO 45
<211> LENGTH: 22
<212> TYPE: DNA
<213> ORGANISM: Artificial Sequence
<220> FEATURE:
<223> OTHER INFORMATION: F1 primer for ACO5

<400> SEQUENCE: 45
aacttcctca caggcagcga gc                                          22

<210> SEQ ID NO 46
<211> LENGTH: 39
<212> TYPE: DNA
<213> ORGANISM: Artificial Sequence
<220> FEATURE:
<223> OTHER INFORMATION: R1 primer for ACO5

<400> SEQUENCE: 46
atggctctct gggcggagta gagagtggga gttgaggtc                        39

<210> SEQ ID NO 47
<211> LENGTH: 34
<212> TYPE: DNA
<213> ORGANISM: Artificial Sequence
<220> FEATURE:
<223> OTHER INFORMATION: F2 primer for ACO5

<400> SEQUENCE: 47
ttgttgtgtt tctcgccccg tcaaggacgc tgag                             34

<210> SEQ ID NO 48
<211> LENGTH: 22
<212> TYPE: DNA
<213> ORGANISM: Artificial Sequence
<220> FEATURE:
<223> OTHER INFORMATION: R2 primer for ACO5

<400> SEQUENCE: 48
acagtaaggt ggggcttgac tc                                          22

<210> SEQ ID NO 49
<211> LENGTH: 21
<212> TYPE: DNA
<213> ORGANISM: Artificial Sequence
<220> FEATURE:
<223> OTHER INFORMATION: F1 primer for ACO6

<400> SEQUENCE: 49
agtccctcaa cacgtttacc g                                           21

<210> SEQ ID NO 50
<211> LENGTH: 46
<212> TYPE: DNA
<213> ORGANISM: Artificial Sequence
<220> FEATURE:
<223> OTHER INFORMATION: R1 primer for ACO6

<400> SEQUENCE: 50
tctttatcct gtctgaaccg gtctgccatt tagtggcagc aacgtt       46

<210> SEQ ID NO 51
<211> LENGTH: 45
<212> TYPE: DNA
<213> ORGANISM: Artificial Sequence
<220> FEATURE:
<223> OTHER INFORMATION: F2 primer for ACO6

<400> SEQUENCE: 51
atcgctacct catatccgca cctccgagct ctgatcaacc gaacc       45

<210> SEQ ID NO 52
<211> LENGTH: 20
<212> TYPE: DNA
<213> ORGANISM: Artificial Sequence
<220> FEATURE:
<223> OTHER INFORMATION: R2 primer for ACO6

<400> SEQUENCE: 52
aggaagggtc taatgacaga       20

<210> SEQ ID NO 53
<211> LENGTH: 17
<212> TYPE: DNA
<213> ORGANISM: Artificial Sequence
<220> FEATURE:
<223> OTHER INFORMATION: F1 primer for FALDH1

<400> SEQUENCE: 53
aatcactcct cctacgc       17

<210> SEQ ID NO 54
<211> LENGTH: 43
<212> TYPE: DNA
<213> ORGANISM: Artificial Sequence
<220> FEATURE:
<223> OTHER INFORMATION: R1 primer for FALDH1

<400> SEQUENCE: 54
tctttatcct gtctgaaccg gtctgtggtc tcggggacac ctc       43

<210> SEQ ID NO 55
<211> LENGTH: 43
<212> TYPE: DNA
<213> ORGANISM: Artificial Sequence
<220> FEATURE:
<223> OTHER INFORMATION: F2 primer for FALDH1

<400> SEQUENCE: 55
atcgctacct catatccgca cctccccatc atcaagcccc gaa       43

<210> SEQ ID NO 56
<211> LENGTH: 20
<212> TYPE: DNA
<213> ORGANISM: Artificial Sequence
<220> FEATURE:
<223> OTHER INFORMATION: R2 primer for FALDH1

<400> SEQUENCE: 56
accgacataa tctgagcaat       20

<210> SEQ ID NO 57
<211> LENGTH: 19
<212> TYPE: DNA
<213> ORGANISM: Artificial Sequence

```
<220> FEATURE:
<223> OTHER INFORMATION: F1 primer for FALDH2

<400> SEQUENCE: 57
accactaggt gagatcgag                                                     19

<210> SEQ ID NO 58
<211> LENGTH: 45
<212> TYPE: DNA
<213> ORGANISM: Artificial Sequence
<220> FEATURE:
<223> OTHER INFORMATION: R1 primer for FALDH2

<400> SEQUENCE: 58
tctttatcct gtctgaaccg gtctgctccg acactaccgg aacgc                        45

<210> SEQ ID NO 59
<211> LENGTH: 43
<212> TYPE: DNA
<213> ORGANISM: Artificial Sequence
<220> FEATURE:
<223> OTHER INFORMATION: F2 primer for FALDH2

<400> SEQUENCE: 59
atcgctacct catatccgca cctcccttgc tcccacagtt gtt                          43

<210> SEQ ID NO 60
<211> LENGTH: 19
<212> TYPE: DNA
<213> ORGANISM: Artificial Sequence
<220> FEATURE:
<223> OTHER INFORMATION: R2 primer for FALDH2

<400> SEQUENCE: 60
gatcacccag aaccatagc                                                     19

<210> SEQ ID NO 61
<211> LENGTH: 19
<212> TYPE: DNA
<213> ORGANISM: Artificial Sequence
<220> FEATURE:
<223> OTHER INFORMATION: F1 primer for FALDH3

<400> SEQUENCE: 61
gtgaccccca ccacgtcac                                                     19

<210> SEQ ID NO 62
<211> LENGTH: 46
<212> TYPE: DNA
<213> ORGANISM: Artificial Sequence
<220> FEATURE:
<223> OTHER INFORMATION: R1 primer for FALDH3

<400> SEQUENCE: 62
tctttatcct gtctgaaccg gtctgttctg acattttcag cgccac                       46

<210> SEQ ID NO 63
<211> LENGTH: 45
<212> TYPE: DNA
<213> ORGANISM: Artificial Sequence
<220> FEATURE:
<223> OTHER INFORMATION: F2 primer for FALDH3

<400> SEQUENCE: 63
atcgctacct catatccgca cctcccccatt acgagcgttt gacgg                       45
```

<210> SEQ ID NO 64
<211> LENGTH: 17
<212> TYPE: DNA
<213> ORGANISM: Artificial Sequence
<220> FEATURE:
<223> OTHER INFORMATION: R2 primer for FALDH3

<400> SEQUENCE: 64
cagggctggg gaccacc                                                    17

<210> SEQ ID NO 65
<211> LENGTH: 19
<212> TYPE: DNA
<213> ORGANISM: Artificial Sequence
<220> FEATURE:
<223> OTHER INFORMATION: F1 primer for FALDH4

<400> SEQUENCE: 65
taccgactgg accagattc                                                  19

<210> SEQ ID NO 66
<211> LENGTH: 46
<212> TYPE: DNA
<213> ORGANISM: Artificial Sequence
<220> FEATURE:
<223> OTHER INFORMATION: R1 primer for FALDH4

<400> SEQUENCE: 66
tctttatcct gtctgaaccg gtctgcggca gtggcaatga tcttac                    46

<210> SEQ ID NO 67
<211> LENGTH: 46
<212> TYPE: DNA
<213> ORGANISM: Artificial Sequence
<220> FEATURE:
<223> OTHER INFORMATION: F2 primer for FALDH4

<400> SEQUENCE: 67
atcgctacct catatccgca cctccgactc gattcatcgc tcctac                    46

<210> SEQ ID NO 68
<211> LENGTH: 21
<212> TYPE: DNA
<213> ORGANISM: Artificial Sequence
<220> FEATURE:
<223> OTHER INFORMATION: R2 primer for FALDH4

<400> SEQUENCE: 68
caaatctttc ggaagattcg g                                               21

<210> SEQ ID NO 69
<211> LENGTH: 20
<212> TYPE: DNA
<213> ORGANISM: Artificial Sequence
<220> FEATURE:
<223> OTHER INFORMATION: F primer for HISG1

<400> SEQUENCE: 69
cagaccggtt cagacaggat                                                 20

<210> SEQ ID NO 70
<211> LENGTH: 20
<212> TYPE: DNA
<213> ORGANISM: Artificial Sequence
<220> FEATURE:
<223> OTHER INFORMATION: R primer for HISG1

```
<400> SEQUENCE: 70
ggaggtgcgg atatgaggta                                                    20

<210> SEQ ID NO 71
<211> LENGTH: 20
<212> TYPE: DNA
<213> ORGANISM: Artificial Sequence
<220> FEATURE:
<223> OTHER INFORMATION: F primer for HISG2

<400> SEQUENCE: 71
aacgctacct cgaccagaaa                                                    20

<210> SEQ ID NO 72
<211> LENGTH: 20
<212> TYPE: DNA
<213> ORGANISM: Artificial Sequence
<220> FEATURE:
<223> OTHER INFORMATION: R primer for HISG2

<400> SEQUENCE: 72
tcttctcgat cggcagtacc                                                    20

<210> SEQ ID NO 73
<211> LENGTH: 20
<212> TYPE: DNA
<213> ORGANISM: Artificial Sequence
<220> FEATURE:
<223> OTHER INFORMATION: F primer for glt2

<400> SEQUENCE: 73
tcagaacttg cgccgataaa                                                    20

<210> SEQ ID NO 74
<211> LENGTH: 22
<212> TYPE: DNA
<213> ORGANISM: Artificial Sequence
<220> FEATURE:
<223> OTHER INFORMATION: R primer for glt2

<400> SEQUENCE: 74
ctttgccagc tagaccatag ag                                                 22

<210> SEQ ID NO 75
<211> LENGTH: 19
<212> TYPE: DNA
<213> ORGANISM: Artificial Sequence
<220> FEATURE:
<223> OTHER INFORMATION: F primer for glt3

<400> SEQUENCE: 75
attggcgggt tcgttactt                                                     19

<210> SEQ ID NO 76
<211> LENGTH: 22
<212> TYPE: DNA
<213> ORGANISM: Artificial Sequence
<220> FEATURE:
<223> OTHER INFORMATION: R primer for glt3

<400> SEQUENCE: 76
cctggaagaa ggccgtatta tc                                                 22

<210> SEQ ID NO 77
```

```
<211> LENGTH: 23
<212> TYPE: DNA
<213> ORGANISM: Artificial Sequence
<220> FEATURE:
<223> OTHER INFORMATION: Ulura3 cs 2B primer for Bipartite

<400> SEQUENCE: 77
atgccctcct acgaagctcg agc                                              23

<210> SEQ ID NO 78
<211> LENGTH: 20
<212> TYPE: DNA
<213> ORGANISM: Artificial Sequence
<220> FEATURE:
<223> OTHER INFORMATION: Ylura3F primer for Bipartite

<400> SEQUENCE: 78
ctcccaacga aagctggcc                                                   20

<210> SEQ ID NO 79
<211> LENGTH: 42
<212> TYPE: DNA
<213> ORGANISM: Artificial Sequence
<220> FEATURE:
<223> OTHER INFORMATION: EXP1-F primer for transaminase vector

<400> SEQUENCE: 79
ccaagcttgg taccgagctc agagtttggc gcccgttttt tc                         42

<210> SEQ ID NO 80
<211> LENGTH: 42
<212> TYPE: DNA
<213> ORGANISM: Artificial Sequence
<220> FEATURE:
<223> OTHER INFORMATION: EXP1-R primer for transaminase vector

<400> SEQUENCE: 80
cgttgttttt gcatatgtgc tgtagatatg tcttgtgtgt aa                         42

<210> SEQ ID NO 81
<211> LENGTH: 42
<212> TYPE: DNA
<213> ORGANISM: Artificial Sequence
<220> FEATURE:
<223> OTHER INFORMATION: TEF-F primer for transaminase vector

<400> SEQUENCE: 81
ccaagcttgg taccgagctc aaactttggc aaagaggctg ca                         42

<210> SEQ ID NO 82
<211> LENGTH: 42
<212> TYPE: DNA
<213> ORGANISM: Artificial Sequence
<220> FEATURE:
<223> OTHER INFORMATION: TEF-R primer for transaminase vector

<400> SEQUENCE: 82
cgttgttttt gcatatgttt gaatgattct tatactcaga ag                         42

<210> SEQ ID NO 83
<211> LENGTH: 44
<212> TYPE: DNA
<213> ORGANISM: Artificial Sequence
<220> FEATURE:
<223> OTHER INFORMATION: ALK1-F primer for transaminase vector

<400> SEQUENCE: 83
```
ccaagcttgg taccgagctc agatctgtgc gcctctacag accc 44

<210> SEQ ID NO 84
<211> LENGTH: 41
<212> TYPE: DNA
<213> ORGANISM: Artificial Sequence
<220> FEATURE:
<223> OTHER INFORMATION: ALK1-R primer for transaminase vector

<400> SEQUENCE: 84
cgttgttttt gcatatgagt gcaggagtat tctggggagg a 41

<210> SEQ ID NO 85
<211> LENGTH: 28
<212> TYPE: DNA
<213> ORGANISM: Artificial Sequence
<220> FEATURE:
<223> OTHER INFORMATION: XPR2t-F2 primer for transaminase vector

<400> SEQUENCE: 85
gtcgacgcaa ttaacagata gtttgccg 28

<210> SEQ ID NO 86
<211> LENGTH: 32
<212> TYPE: DNA
<213> ORGANISM: Artificial Sequence
<220> FEATURE:
<223> OTHER INFORMATION: XPR2t-R3 primer for transaminase vector

<400> SEQUENCE: 86
ctcgagggat cccggaaaac aaaacacgac ag 32

<210> SEQ ID NO 87
<211> LENGTH: 28
<212> TYPE: DNA
<213> ORGANISM: Artificial Sequence
<220> FEATURE:
<223> OTHER INFORMATION: TA-F primer for transaminase vector

<400> SEQUENCE: 87
catatgcaaa aacaacgtac tacctccc 28

<210> SEQ ID NO 88
<211> LENGTH: 28
<212> TYPE: DNA
<213> ORGANISM: Artificial Sequence
<220> FEATURE:
<223> OTHER INFORMATION: TA-R primer for transaminase vector

<400> SEQUENCE: 88
gtcgacttag gccaaaccac gggctttc 28

<210> SEQ ID NO 89
<211> LENGTH: 35
<212> TYPE: DNA
<213> ORGANISM: Artificial Sequence
<220> FEATURE:
<223> OTHER INFORMATION: ATATG2-ER-F primer for transaminase vector

<400> SEQUENCE: 89
actcctgcac tcatatgtcc aacgccctca acctg 35

<210> SEQ ID NO 90
<211> LENGTH: 35
<212> TYPE: DNA

<210> SEQ ID NO 90
<211> LENGTH: 35
<212> TYPE: DNA
<213> ORGANISM: Artificial Sequence
<220> FEATURE:
<223> OTHER INFORMATION: XTATG2-ER-F primer for transaminase vector

<400> SEQUENCE: 90
ccaatccaac acatatgtcc aacgccctca acctg         35

<210> SEQ ID NO 91
<211> LENGTH: 82
<212> TYPE: DNA
<213> ORGANISM: Artificial Sequence
<220> FEATURE:
<223> OTHER INFORMATION: ER-R-1 primer for transaminase vector

<400> SEQUENCE: 91
cgttgttttt gcatagaacc gccaccgccg ctaccgccac cgcccgaacc gccaccgccg    60
aatcgtgaaa tatccttggg ct         82

<210> SEQ ID NO 92
<211> LENGTH: 85
<212> TYPE: DNA
<213> ORGANISM: Artificial Sequence
<220> FEATURE:
<223> OTHER INFORMATION: ER-R-2 primer for transaminase vector

<400> SEQUENCE: 92
cgttgttttt gcatatgaga accgccaccg ccgctaccgc caccgcccga accgccaccg    60
ccgaatcgtg aaatatcctt gggct         85

<210> SEQ ID NO 93
<211> LENGTH: 37
<212> TYPE: DNA
<213> ORGANISM: Artificial Sequence
<220> FEATURE:
<223> OTHER INFORMATION: ETATG2-ER-1 primer for transaminase vector

<400> SEQUENCE: 93
tgattacgcc aagcttgagt ttggcgcccg ttttttc         37

<210> SEQ ID NO 94
<211> LENGTH: 50
<212> TYPE: DNA
<213> ORGANISM: Artificial Sequence
<220> FEATURE:
<223> OTHER INFORMATION: ETATG2-ER-2 primer for transaminase vector

<400> SEQUENCE: 94
acaggttgag ggcgttggac atatgtgctg tagatatgtc ttgtgtgtaa         50

<210> SEQ ID NO 95
<211> LENGTH: 36
<212> TYPE: DNA
<213> ORGANISM: Artificial Sequence
<220> FEATURE:
<223> OTHER INFORMATION: TTATG2-ER-1 primer for transaminase vector

<400> SEQUENCE: 95
tgattacgcc aagcttaaac tttggcaaag aggctg         36

<210> SEQ ID NO 96
<211> LENGTH: 50
<212> TYPE: DNA
<213> ORGANISM: Artificial Sequence
<220> FEATURE:
<223> OTHER INFORMATION: TTATG2-ER-2 primer for transaminase vector

<400> SEQUENCE: 96
acaggttgag ggcgttggac atatgtttga atgattctta tactcagaag　　　　　50

<210> SEQ ID NO 97
<211> LENGTH: 21
<212> TYPE: DNA
<213> ORGANISM: Artificial Sequence
<220> FEATURE:
<223> OTHER INFORMATION: ER-F primer for transaminase vector

<400> SEQUENCE: 97
atgtccaacg ccctcaacct g　　　　　21

<210> SEQ ID NO 98
<211> LENGTH: 34
<212> TYPE: DNA
<213> ORGANISM: Artificial Sequence
<220> FEATURE:
<223> OTHER INFORMATION: ER-R-3 primer for transaminase vector

<400> SEQUENCE: 98
cgttgttttt gcatagaacc gccaccgccg ctac　　　　　34

<210> SEQ ID NO 99
<211> LENGTH: 19
<212> TYPE: DNA
<213> ORGANISM: Artificial Sequence
<220> FEATURE:
<223> OTHER INFORMATION: TA-FALDH4-F1 primer for transaminase vector

<400> SEQUENCE: 99
taccgactgg accagattc　　　　　19

<210> SEQ ID NO 100
<211> LENGTH: 21
<212> TYPE: DNA
<213> ORGANISM: Artificial Sequence
<220> FEATURE:
<223> OTHER INFORMATION: TA-FALDH4-R1 primer for transaminase vector

<400> SEQUENCE: 100
cggcagtggc aatgatctta c　　　　　21

<210> SEQ ID NO 101
<211> LENGTH: 45
<212> TYPE: DNA
<213> ORGANISM: Artificial Sequence
<220> FEATURE:
<223> OTHER INFORMATION: TA-FALDH4-F2 primer for transaminase vector

<400> SEQUENCE: 101
ctcctctatg gtctagctgg caaagactcg attcatcgct cctac　　　　　45

<210> SEQ ID NO 102
<211> LENGTH: 21
<212> TYPE: DNA
<213> ORGANISM: Artificial Sequence
<220> FEATURE:
<223> OTHER INFORMATION: TA-FALDH4-R2 primer for transaminase vector

<400> SEQUENCE: 102
caaatctttc ggaagattcg g　　　　　21

<210> SEQ ID NO 103

```
<211> LENGTH: 47
<212> TYPE: DNA
<213> ORGANISM: Artificial Sequence
<220> FEATURE:
<223> OTHER INFORMATION: ATATG2-F primer for transaminase vector

<400> SEQUENCE: 103
gtcggtaaga tcattgccac tgccgagatc tgtgcgcctc tacagac          47

<210> SEQ ID NO 104
<211> LENGTH: 46
<212> TYPE: DNA
<213> ORGANISM: Artificial Sequence
<220> FEATURE:
<223> OTHER INFORMATION: ETATG2-F primer for transaminase vector

<400> SEQUENCE: 104
gtcggtaaga tcattgccac tgccggagtt tggcgcccgt tttttc           46

<210> SEQ ID NO 105
<211> LENGTH: 46
<212> TYPE: DNA
<213> ORGANISM: Artificial Sequence
<220> FEATURE:
<223> OTHER INFORMATION: TTATG2-F primer for transaminase vector

<400> SEQUENCE: 105
gtcggtaaga tcattgccac tgccgaaact ttggcaaaga ggctgc           46

<210> SEQ ID NO 106
<211> LENGTH: 45
<212> TYPE: DNA
<213> ORGANISM: Artificial Sequence
<220> FEATURE:
<223> OTHER INFORMATION: XTATG2-F primer for transaminase vector

<400> SEQUENCE: 106
gtcggtaaga tcattgccac tgccgacgcg tggagagttt gggtt            45
```